United States Patent [19]
Mochizuki et al.

[11] Patent Number: 5,965,743

[45] Date of Patent: *Oct. 12, 1999

[54] N-SUBSTITUTED IMIDAZOL DERIVATIVE

[75] Inventors: Nobuo Mochizuki; Seiichi Uchida, both of Kanagawa; Izumi Kumita, Tokyo; Hiroyuki Miyamoto, Niigata; Hiromi Ichihara, Kanagawa, all of Japan

[73] Assignee: Nippon Soda Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/732,232

[22] PCT Filed: Apr. 26, 1996

[86] PCT No.: PCT/JP95/00827

§ 371 Date: Mar. 3, 1997

§ 102(e) Date: Mar. 3, 1997

[87] PCT Pub. No.: WO95/29163

PCT Pub. Date: Nov. 2, 1995

[30] Foreign Application Priority Data

| Apr. 27, 1994 | [JP] | Japan | 6-111952 |
| Aug. 5, 1994 | [JP] | Japan | 6-204421 |
| Aug. 30, 1994 | [JP] | Japan | 6-228940 |
| Nov. 24, 1994 | [JP] | Japan | 6-314094 |
| Nov. 25, 1994 | [JP] | Japan | 6-315631 |

[51] Int. Cl.⁶ ...... C07D 233/58; C07D 233/60; C07D 233/61; A61K 31/415

[52] U.S. Cl. ...... 548/335.5; 548/336.1; 548/340.1; 548/341.1; 548/343.5; 548/346.1; 514/399; 514/400

[58] Field of Search ...... 548/335.5, 341.1, 548/336.1, 340.1, 343.5, 346.1

[56] References Cited

U.S. PATENT DOCUMENTS

| 3,941,802 | 3/1976 | Gall | 548/343.5 |
| 4,006,243 | 2/1977 | Strehlke et al. | 424/273 |
| 4,301,169 | 11/1981 | Yamanaka et al. | 424/273 R |
| 4,328,348 | 5/1982 | Ogata et al. | 548/346.1 X |
| 4,440,774 | 4/1984 | Baldwin | 424/267 |
| 4,463,001 | 7/1984 | Melloni et al. | 424/246 |
| 4,463,011 | 7/1984 | Ogata et al. | 424/273 R |
| 4,916,144 | 4/1990 | Strehlke et al. | 514/326 |

FOREIGN PATENT DOCUMENTS

| 2-197839 | of 0000 | Japan . |
| 6-199791 | of 0000 | Japan . |
| 60-18654 | of 0000 | Japan . |
| 50-148357 | 11/1975 | Japan . |
| 52-83557 | 7/1977 | Japan . |
| 55-69567 | 5/1980 | Japan . |
| 55-100368 | 7/1980 | Japan . |
| 55-164677 | 12/1980 | Japan . |
| 63-23868 | 2/1988 | Japan . |
| 63-119425 | 5/1988 | Japan . |

Primary Examiner—Floyd D. Higel
Attorney, Agent, or Firm—Jacobson, Price, Holman & Stern, PLLC

[57] ABSTRACT

The present invention is to provide novel imidazole derivatives effectual as an antihyperlipemic agent and therapeutic and preventive drugs for arteriosclerosis, and to provide methods for manufacturing the said derivatives.

More particularly, the present invention is directed to the compounds represented by the following general formula [I];

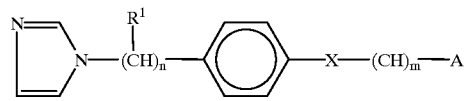

wherein $R^1$ is hydrogen or lower alkyl, n is 0 or 1, X is N-$r^1$ wherein $r^1$ is hydrogen or lower alkyl, O, S, SO, $SO_2$, $CH_2$, $CH(CH_3)$, CONH or $C(r^2)$=NO wherein $r^2$ is hydrogen or lower alkyl, m is 0 or an integer of from 1 to 12, and A is methyl or a group represented by the following general formula;

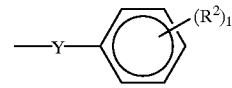

wherein Y is N-$r^3$ wherein $r^3$ is hydrogen or lower alkyl, N($r^4$)$SO_2$ wherein $r^4$ is hydrogen or lower alkyl, O, S, SO, $SO_2$, $CH_2$, $CH(CH_3)$, CONH or $C(r^5)$=NO wherein $r^5$ is hydrogen or lower alkyl, $R^2$ is a halogen, a lower alkyl, a lower alkoxy, a cycloalkyl or COO$r^6$ wherein $r^6$ is hydrogen or a lower alkyl, and l is 0, 1, 2 or 3, however, m denotes an integer of from 6 to 9 when A is methyl, or m denotes 0 or an integer of from 1 to 6 when A is a group represented by the following general formula;

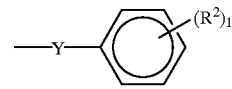

and X and Y are each independently $CH_2$ when m is 0, the pharmaceutically-acceptable salts thereof and methods for manufacturing the said compounds and the pharmaceutically-acceptable salts thereof.

13 Claims, No Drawings

N-SUBSTITUTED IMIDAZOL DERIVATIVE

This application is a 371 of PCT/JP95/00827, filed Apr. 26, 1996.

FIELD OF THE INVENTION

The present invention relates to novel imidazole derivatives effectual as an antihyperlipemic agent and therapeutic and preventive drugs for arteriosclerosis and methods for manufacturing the said imidazole derivatives.

BACKGROUND ART

In recent years, antihyperlipemic agents, which inhibit the biosynthesis of cholesterol and neutral lipids, which are both influential as the inducing cause of arteriosclerosis and other diseases, have attracted considerable attention.

As the representative drugs for such diseases, pravastatin and simvastatin are presently known.

As the similar compounds to the compounds of the present invention, the following compounds are disclosed as an antimicrobial agent in Japanese Patent Publication No. Sho 60-18654,

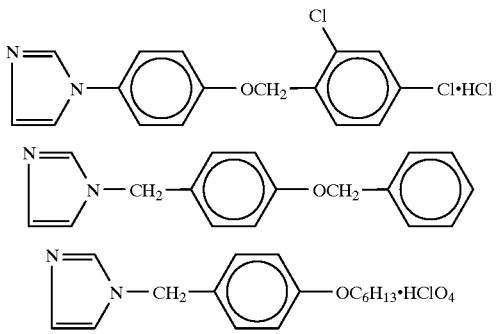

and the following compound is disclosed as an preventive agent for decoloration in Japanese Patent Laid-opened No. Hei 2-197839,

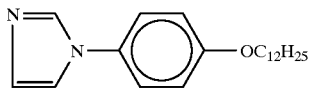

and further, the following compound is disclosed as an anti-allergic agent in Japanese Patent Laid-opened No. Hei 6-199791.

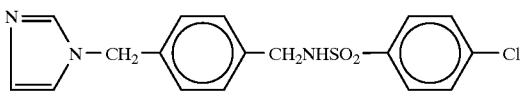

It is an object of the present invention to provide novel imidazole derivatives, which are excellently effective on hyperlipemia, having therapeutic and preventive effect on arteriosclerosis, safe, and causing less side effect, and to provide advantageous methods for manufacturing the said imidazole derivatives in an industrial scale.

DISCLOSURE OF THE INVENTION

The present invention is directed to the compounds represented by the following general formula [I];

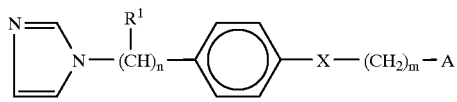

wherein $R^1$ is hydrogen or lower alkyl, n is 0 or 1, X is N-$r^1$ wherein $r^1$ is hydrogen or lower alkyl, O, S, SO, $SO_2$, $CH_2$, $CH(CH_3)$, CONH or $C(r^2)=NO$ wherein $r^2$ is hydrogen or lower alkyl, m denotes 0 or an integer of from 1 to 12, and A is methyl or a group represented by the following general formula;

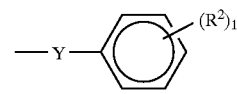

wherein Y is N-$r^3$ wherein $r^3$ is hydrogen or lower alkyl, $N(r^4)SO_2$ wherein $r^4$ is hydrogen or lower alkyl, O, S, SO, $SO_2$, $CH_2$, $CH(CH_3)$, CONH or $C(r^5)=NO$ wherein $r^5$ is hydrogen or lower alkyl, $R^2$ is halogen, lower alkyl, lower alkoxy, cycloalkyl or $COOr^6$ wherein $r^6$ is hydrogen or lower alkyl, and l is 0, 1, 2 or 3, however m denotes an integer of from 6 to 9 when A is methyl, or m denotes 0 or an integer of from 1 to 6 when A is a group represented by the following general formula;

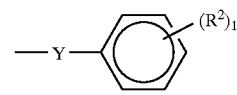

and X and Y is each independently $CH_2$ when m is 0, the pharmaceutically-acceptable salts thereof and methods for manufacturing the said compounds and the said pharmaceutically acceptable salts.

For examples of the pharmaceutically-acceptable salts of the present invention, inorganic acids, such as hydrochloric acid, sulfuric acid, nitric acid and phosphoric acid, organic acids, such as acetic acid, propionic acid, lactic acid succinic acid, tartaric acid, citric acid, benzoic acid, salicylic acid, nicotitic acid and heptagluconic acid, can be given.

In the present invention, for examples of the lower alkyl represented by the substituents, $R^1$, $R^2$, $r^1$, $r^2$, $r^3$, $r^4$, $r^5$ and $r^6$, straight-chain or branched alkyl having 1 to 6 carbon atoms, preferably methyl, ethyl, propyl, isopropyl, butyl, isobutyl, sec-butyl and t-butyl, can be given. The halogen represented by the substituent $R^2$ may be any of fluorine, chlorine, bromine and iodine, and the lower alkoxy represented by the substituent $R^2$ is straight-chain or branched alkoxy having 1 to 6 carbon atoms, preferably any of methoxy, ethoxy, propoxy, isopropoxy, butoxy, isobutoxy, t-butoxy and sec-butoxy. And, the cycloalkyl represented by $R^2$ is the ones containing 3 to 7 carbon atoms.

The compounds of the present invention can be manufactured according to the following manufacturing methods.

[1] When manufacturing the compound represented by the general formula [I] where in n is 0;

(1) And, wherein X is N-$r^1$, O, S or C($r^2$)=NO:

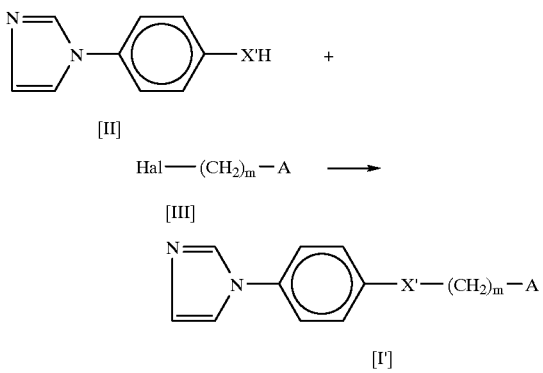

[II]

Hal—(CH$_2$)$_m$—A

[III]

[I']

wherein X' is N-$r^1$, O, S or C($r^2$)=NO and Hal denotes an halogen atom.

The reaction represented by the reaction formula as shown hereinabove is carried out for from 30 min. to several dozen of hours at a temperature of from −20° C. to the boiling point of a solvent used, and preferably from room temperature to nearly 50° C., in an inactive solvent, such as N,N-dimethylformamide(DMF), tetrahydrofuran(THF) and hexamethylphosphoramide(HMPA), in the presence of alkali, such as sodium hydride, sodium ethoxide and potassium t-butoxide.

When X is N-$r^1$ and $r^1$ is hydrogen, however, the reaction is preferably carried out after protecting one of hydrogen atoms with a group such as formyl in order to prevent the occurrence of the side reaction.

The compounds represented by the general formulas [II] and [III] shown above can be manufactured according to the following reaction formula, for example.

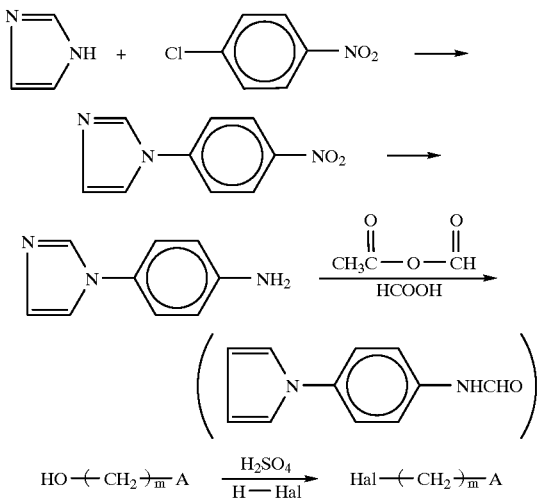

Whereas, the compounds, wherein X is SO or SO$_2$, can be manufactured by oxidizing the corresponding thio ether compound with an appropriate oxidizing agent, such as hydrogen peroxide, peracetic acid and m-chloroperbenzoic acid.

(2) Wherein X is CH$_2$ or CH(CH$_3$):

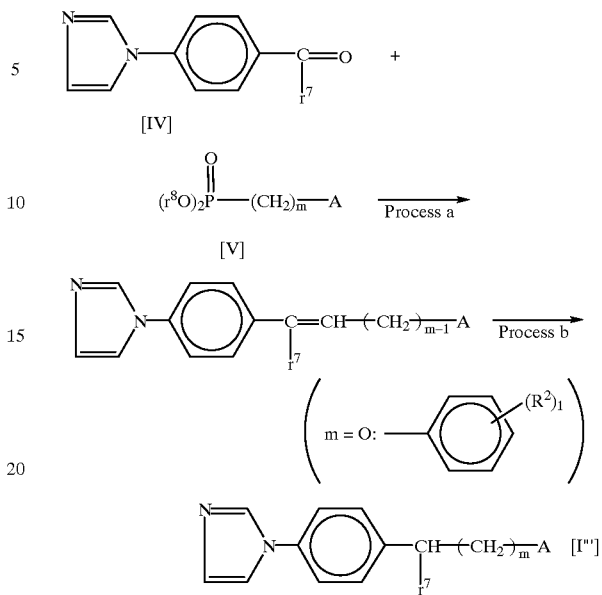

[IV]

($r^8$O)$_2$P—(CH$_2$)$_{\overline{m}}$—A

[V]

Process a

Process b

[I''']

wherein $r^7$ is hydrogen or methyl and $r^8$ is lower alkyl.

The reaction according to the Process a is normally carried out under the condition established for Wittig-Horner reaction. More particularly, the reaction is carried out for from 30 min. to several dozen of hours in an inactive solvent, such as THF and 1,2-dimethoxyethane(DME), at a temperature of from −20° C. to 50° C., and preferably from −5° C. to nearly room temperature, in the presence of alkali, such as sodium hydride, potassium t-butoxide and potassium carbonate, and preferably under atmosphere of an inactive gas, such as nitrogen gas.

After completed the reaction, the intermediate can be isolated according to a procedure for post-treatment generally known, and a reducing reaction according to the Process b is subsequently carried out. Namely, the objective compound can be obtained through normal procedure for contact reduction by using a catalyzer, such as palladium or the like.

(3) Wherein A is Y'—C$_6$H$_{5-1}$(R$^2$)$_1$:

The compounds of the present invention can be manufactured according to the following reaction formula;

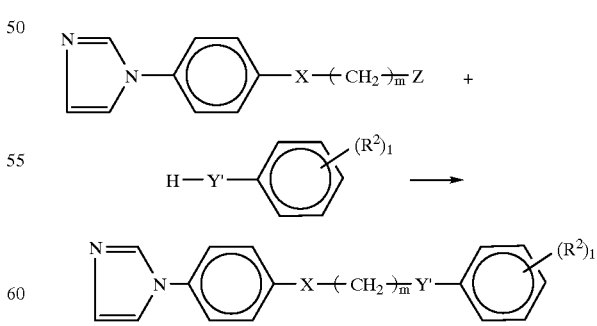

wherein Z is halogen or an eliminating group, such as CH$_3$SO$_2$O and p—Me—Ph—SO$_2$O, and Y' is NH, O or S.

[2] When manufacturing the compound represented by the general formula [I] wherein n is 1;

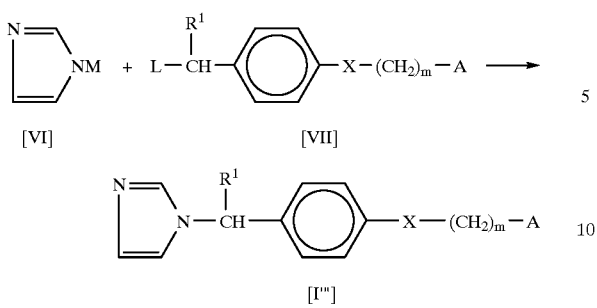

wherein $R^1$, X, m and A are as described above, M is hydrogen or an alkali metal, and L is an eliminating group.

For the preferable eliminating groups represented by L, halogen, such as chlorine and bromine, sulfonyloxy, such as methanesulfonyloxy and p-toluenesulfonyloxy, and hydroxy can be exemplified.

The reaction of imidazole compounds represented by a general formula [VI] and the compounds represented by a general formula [VII] is taken place in an organic solvent, such as aromatic hydrocarbons including benzene and toluene, ethers including diethyl ether, dioxane, tetrahydrofuran and 1,2-dimethoxyethane, alcohols including ethanol, amides including dimethylformamide and triamide hexamethylphosphate or in water at a temperature of from 0 to the boiling point of the solvent used, and preferably from room temperature to the boiling point of the solvent used, or without solvent, at a temperature of from 80 to 200° C., and preferably from 100 to 180° C., in or without the presence of a catalyzer, such as p-toluenesulfonic acid, copper powder and iodinated alkali.

The imidazole compounds can be used in a form of free or the alkali salts obtainable from the neutralizing reaction between the imidazole compound and any of hydrogenated alkali, alkali amides, alkali alcoholate, alkali hydroxides, etc.

Alternatively, the said reaction can be carried out by reacting a free imidazole compound with a compound represented by the general formula [VII] in the solvent recited hereinabove at a temperature of from 0 to the boiling point of the solvent used, and preferably from room temperature to the boiling point of the solvent used, in the presence of a base, such as alkali carbonates.

The compound represented by the general formula [VII] can be manufactured according to any of the following reaction formulas, for example;

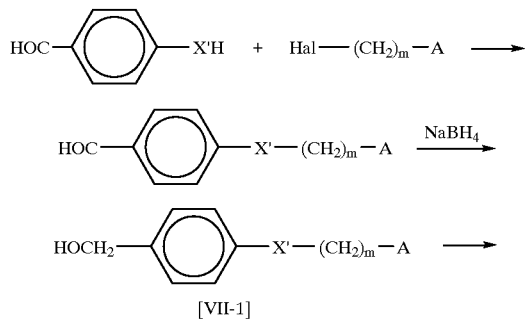

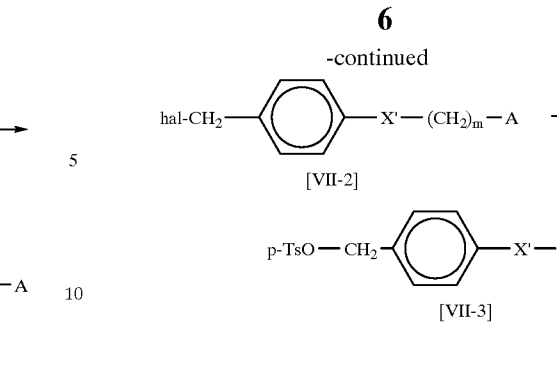

wherein X' is $N-r^1$, O, S or $C(r^2)=NO$, Hal and hal are each independently an halogen atom, and $r^1$ and $r^2$ are each independently hydrogen or lower alkyl, and,

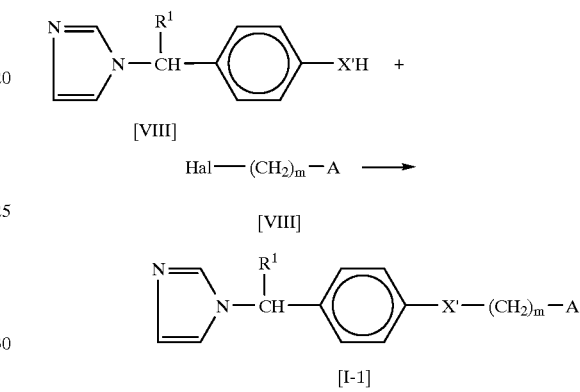

wherein X' is $N-r^1$, O, S or $C(r^2)=NO$, Hal is halogen, and $r^1$ and $r^2$ are as described above.

The reactions are carried out for from 30 min. to several dozen of hours in an inactive organic solvent, such as DMF, at a temperature of from −20° C. to the boiling point of the solvent used, and more preferably at from room temperature up to a temperature under mild heating condition, in the presence of alkali, such as sodium hydride.

When X is $N-r^1$ and $r^1$ is hydrogen, although the reactions can proceed without taking a procedure to protect hydrogens in the compound represented by the general formula [VII], it is yet preferable to protect one of the hydrogens with formyl or the like before the initiation of the reaction in order to prevent the occurence of side reaction and then to remove the protecting group after completed the reaction.

The compounds represented by the general formulas [VIII] and [III] can be manufactured according to the following reaction formula.

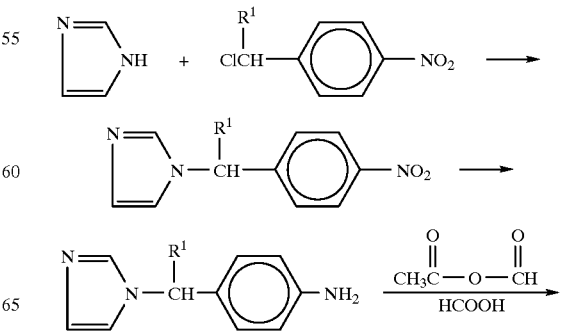

-continued

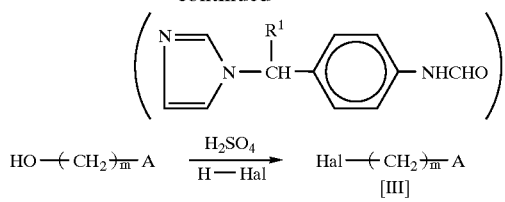

Whereas, the compound represented by the general formula [I], wherein X is SO or $SO_2$, can be manufactured by oxidizing the corresponding thio ether compound.

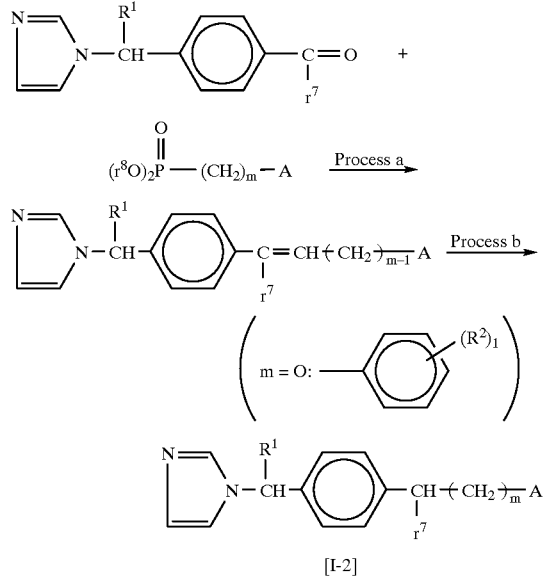

wherein $r^7$ is hydrogen or methyl and $r^8$ is lower alkyl.

The reaction in the process a described above is carried out under ordinary condition established for Wittig-Horner reaction, that is, the reaction is carried out in an organic solvent, such as THF, for a duration of from 30 min. to several dozen of hours at a temperature of from −20 to 50° C., and preferably from −5° C. to near room temperature, in the presence of a base, such as sodium hydride and preferably under atmosphere of an inactive gas, such as nitrogen gas.

After completed the reaction, the intermediate is separated according to the procedure normally used for the post-treatment and is allowed to the process b where the reducing reaction and other reaction be carried out for the intermediate.

In the reaction described above, the objective compound can be obtained after allowing the intermediate to a normal contact reduction by using palladium or the like.

When A is $Y'—C_6H_{5-1}(R^2)_1$, the compound of the present invention can be manufactured according to the following reaction formula.

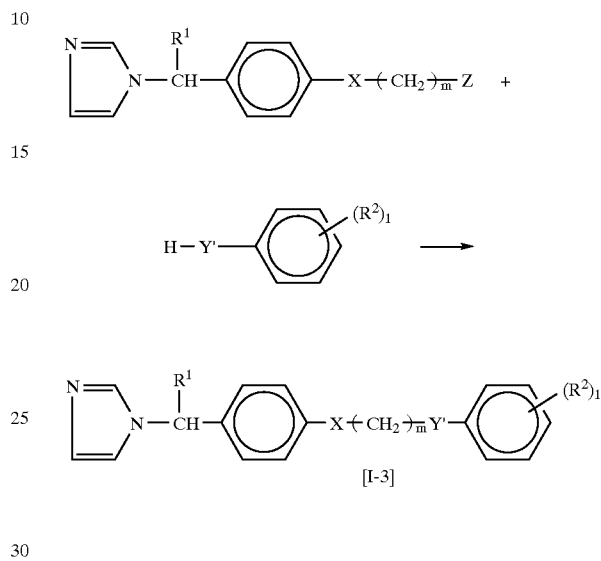

wherein Z is an eliminating group, such as halogen and $CH_3SO_2O$, and Y' is NH, O or S.

Further, the said compound wherein $R^2$ is —COOH can be manufactured according to the following reaction formula.

wherein $r^{6'}$ is lower alkyl.

The objective compound can be obtained by taking the procedure normally used for the post-treatment irrespective to the reaction formula employed for manufacturing the compound of the present invention.

The chemical structure of the compound of the present invention is determined basing on the analytical data obtained by IR, NMR and MASS and the other analytical means.

Best Mode for Carrying Out the Invention

Now, the present invention is further described in detail with referring to the examples as exemplified hereinbelow.

EXAMPLE 1

Manufacturing of 1-[4-(4-phenylbutoxy)phenyl]imidazole

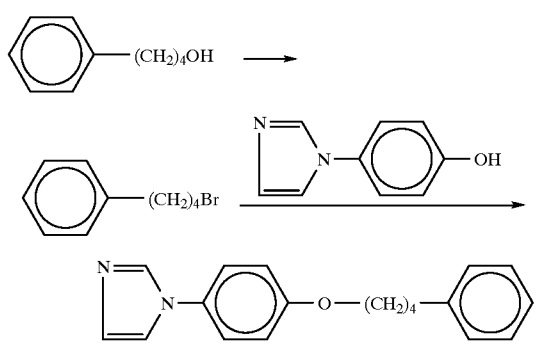

To 1.0 g of 4-phenyl-1-butanol, were added 0.33 g of concentrated sulfuric acid and 1.7 g of 47% aqueous solution of hydrobromic acid, and the resultant solution was then stirred for 5 hours at a temperature of from 140 to 150° C. while applying heating. The solution reacted was then poured into ice water and extracted with ethyl acetate. The organic layer resulted was dried with anhydrous magnesium sulfate, and the solvent used was removed by distillation under reduced pressure, thereby affording 1.25 g of 4-phenyl-1-bromobutane.

0.5 g of 4-(imidazole-1-yl)phenol were added to 20 ml of DMF, and 0.14 g of 60% NaH were subsequently added thereto while cooling the solution with ice. After stirring the solution for 1 hour at room temperature, 0.73 g of 1-phenyl-4-bromobutane obtained hereinabove was fed dropwise to the solution while cooling it with ice. After completed the dropping, the solution was stirred for 2 hours at room temperature and further stirred for a night at a temperature of from 50 to 60° C. The solution reacted was then poured into ice-water and extracted with ethyl acetate. The organic layer resulted was dried with anhydrous magnesium sulfate, and the solvent used was removed by distillation under reduced pressure The residue obtained was purified by using silica gel column chromatography, for which a mixed developer composed of hexane and ethyl acetate (mixing ratio, 1:1) was used, thereby affording 0.8 g of the objective compound with a melting point of 55–56° C.

EXAMPLE 2

Manufacturing of 1-[4-(4-phenylbutylamino)phenyl] imidazole

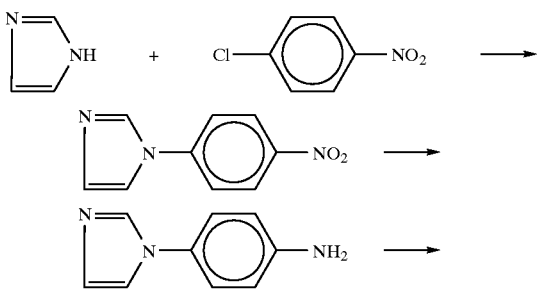

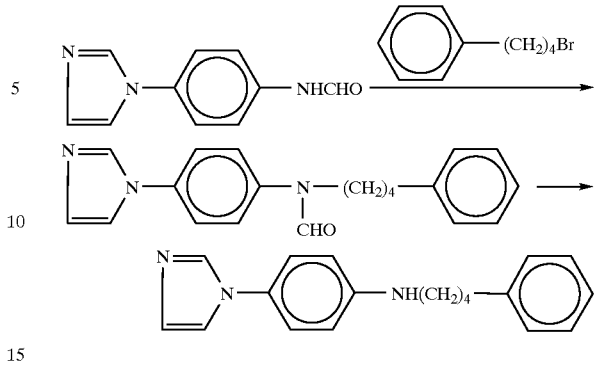

9.5 g of imidazole were dissolved in 100 ml of DMF, and the resultant solution was further added with 6.1 g of 60% NaH while cooling it with ice. The solution was then stirred for 30 min. and further for 1 hour at room temperature. Then, the solution was added with 20.0 g of 4-chloronitrobenzene and then stirred for 2 hours at a temperature of from 80 to 85° C. The solution reacted was poured into ice water, and the crystals precipitated was filtered and then dried to obtain 22.5 g of 4-(imidazole-1-yl)nitrobenzene.

10.0 g of 4-(imidazole-1-yl)nitrobenzene were dissolved in 80 ml of acetic acid, and 35.1 g of anhydrous tin(II) chloride were subsequently added to the resultant solution. The solution was then stirred for 3 hours at 90–95° C. After cooling the solution reacted and removing the solvent used by distillation under reduced pressure, pH of the solution was adjusted to a range of from 9 to 11 with 10% aqueous solution of NaOH to extract the solution with chloroform. After dried the organic layer resulted with anhydrous magnesium sulfate, the solvent used was removed by distillation under reduced pressure, thereby affording 7.2 g of 4-(imidazole-1-yl)aniline.

2.95 g of 4-(imidazole-1-yl)aniline were dissolved in 30 ml of formic acid, and the resultant solution was fed dropwise with 4.9 g of acetic formic anhydride while cooling the solution with ice. Then, the solution was stirred for 1 hour at 0–5° C. and further for 1 hour at room temperature. The product with a low melting point was removed from the solution by distillation under reduced pressure. Then, the solution was neutralized with 10% aqueous solution of NaOH for carrying out the extraction with ethyl acetate. After dried the organic layer resulted with anhydrous magnesium sulfate, the residue obtained by the distillation of the organic layer under reduced pressure was washed with a mixture of ether and hexane, thereby affording 2.5 g of N-formyl-4-(imidazole-1-yl)aniline.

0.4 g of N-formyl-4-(imidazole-1-yl)aniline were dissolved in 20 ml of DMF, and 0.1 g of 60% NaH were further added thereto while cooling the solution with ice. The solution was then stirred for 1 hour at room temperature. To the solution, 0.5 g of 1-phenyl-4-bromo ethane were further fed dropwise, then the solution was stirred for 1 hour at room temperature and further for a night at 50–60° C. The solution reacted was then poured into ice-water and extracted with ethyl acetate. The organic layer resulted was dried with anhydrous magnesium sulfate, and the solvent used was removed by distillation under reduced pressure, thereby affording 0.66 g of the residue.

The residue was dissolved in 30 ml of ethanol, and the resultant solution was then subjected to reflux for 30 min. under heating following to the addition of 30 ml of 10% aqueous solution of NaOH to the solution. After cooling the solution reacted and removing the solvent from the solution by distillation under reduced pressure, the solution was added with water and extracted with ethyl acetate. The organic layer resulted was dried with anhydrous magnesium sulfate, and the solvent used was removed by distillation under reduced pressure. The residue obtained was purified by using silica gel column chromatography, for which a mixture of hexane and ethyl acetate (mixing ratio; 1:1) was used for the developer, thereby affording 0.3 g of the objective compound with a refractive index of $n_D^{24.0}$ 1.600.

EXAMPLE 3

Manufacturing of 1-[4-(2-phenethyl)phenyl]imidazole

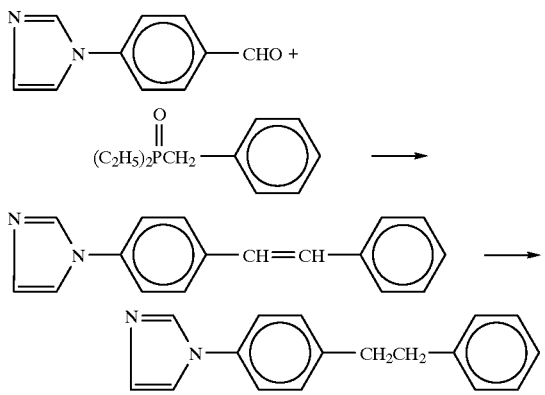

1.0 g of diethylbenzylphosphonate were dissolved in 50 ml of dry THF under nitrogen gas flow. To this solution, were added 0.21 g of 60% NaH while cooling the solution with ice, and the resultant solution was then stirred for 2 hours at room temperature. After cooling the whole solution with ice, 0.75 g of 4-(imidazole-1-yl)benzaldehyde were added thereto and stirred for 48 hours at room temperature. The solution reacted was condensed under reduced pressure, added with water, and extracted with chloroform. The organic layer resulted was dried with anhydrous magnesium sulfate, and the solvent used was removed by distillation under reduced pressure. The residue obtained was purified by using silica gel column chromatography, for which chloroform is used for the developer, thereby affording 0.5 g of 4-(imidazole-1-yl)stilbene.

0.5 g of 4-(imidazole-1-yl)stilbene were dissolved in 30 ml of ethanol, and 0.2 g of 5% palladium-carbon were further added to the resultant solution. The solution was then stirred for 16 hours under normal pressure at room temperature and under an atmosphere being filled with hydrogen gas.

The solution reacted was filtered, and the residue obtained by condensation of the filtrate was dissolved in ethyl acetate and then washed. After drying the organic layer resulted with anhydrous magnesium sulfate, the solvent used was removed by distillation under reduced pressure. The residue obtained was further washed with hexane, thereby affording 0.22 g of the objective compound with a melting point of 85–86° C.

EXAMPLE 4

Manufacturing of 1-[4-(3-phenylpropyloxyiminomethyl)phenyl]imidazole

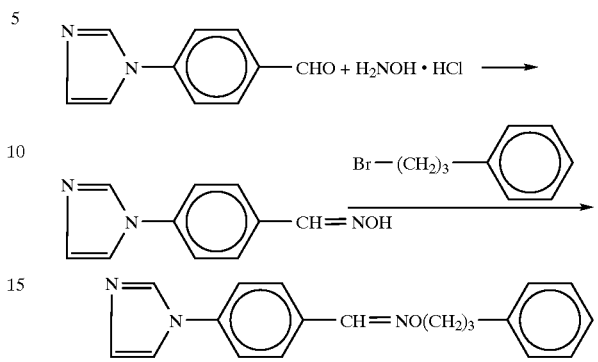

1.5 g of 4-(1-imidazolyl)-benzaldehyde were dissolved in 50 ml of ethanol. To this solution, were added 1.27 g of hydroxyl amine hydrochloride and 1.0 g of aqueous solution of sodium carbonate, and the resultant solution was then subjected to reflux under heating for 1 hour. After completed the reaction, the solution reacted was extracted with ethyl acetate after removing the solvent used by distillation under reduced pressure. The organic layer resulted was washed with water, dried with sodium sulfate, and then condensed under reduced pressure to thereby obtain 1.0 g of the crystals of the oxime compound.

0.6 g of the oxime compound obtained hereinabove were dissolved in 20 ml of DMF, and 0.14 g of 60% NaH were further added to the resultant solution while maintaining the solution at 0° C., then the solution was stirred for 2 hours at room temperature. To the solution, 0.61 g of phenylpropylbromide were further added while cooling, then the solution was allowed to a reaction for 3 hours at room temperature. The solution reacted was poured into ice-water and extracted with ethyl acetate, and the solvent used was distillated under reduced pressure. The residue obtained was separated and purified by using silica gel column chromatography, thereby affording 0.41 g of crystals with a melting point of 62–63° C.

EXAMPLE 5

Manufacturing of 1-[4-(3-phenylpropyloxy)benzyl]imidazole

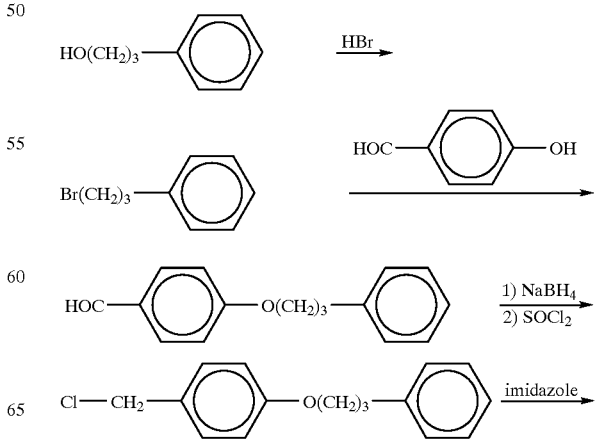

-continued

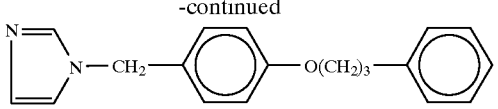

To 3.2 g of 3-phenyl-1-propanol, were added 1.2 g of concentrated sulfuric acid and 6.08 g of 47% aqueous solution of hydrobromic acid, and the resultant solution was heated for 5 hours at 140–150° C. Then, the solution was poured into ice-water and extracted with ethyl acetate. The organic layer resulted was dried with anhydrous magnesium sulfate, and the solvent used was distillated under reduced pressure, thereby affording 4.3 g of 3-phenyl-1-bromopropane.

2.77 g of 4-hydroxybenzaldehyde were dissolved in 30 ml of DMF, and 0.95 g of 60% NaH were further added to the resultant solution. The solution was then stirred for 1 hour after elevating the temperature of the solution up to room temperature. After cooling the solution with ice, 4.3 g of 3-phenyl-1-bromopropane were fed dropwise thereto and the solution was then further stirred for 1 hour at room temperature and subsequently for a night at 50–60° C. The solution reacted was poured into ice-water, extracted with ethyl acetate, then the organic layer resulted was dried with anhydrous magnesium sulfate. Then, the solvent used was distillated under reduce pressure, and the residue obtained was purified by using silica gel column chromatography, for which a mixture of hexane and ethyl acetate (mixing ratio, 4:1) was used for the developer, thereby affording 4.9 g of 4-(3-phenylpropyloxy)benzaldehyde.

4.9 g of 4-(3-phenylpropyloxy)benzaldehyde were dissolved in 30 ml of ethanol, and 0.39 g of sodium borohydride were added to the resultant solution, then the solution was stirred for 1 hour at room temperature. After completed the reaction, the solvent used was distillated under reduced pressure, and the residue obtained was dissolved in a mixture of ethyl acetate and dilute hydrochloric acid. After washing the ethyl acetate layer with dilute hydrochloric acid, dilute alkaline aqueous solution and water in series, the organic layer was then dried with anhydrous magnesium sulfate, and the solvent used was distillated under reduced pressure, thereby affording 4.1 g of 4-(3-phenylpropyloxy) benzyl alcohol.

3.0 g of 4-(3-phenylpropyloxy)benzyl alcohol were dissolved in 30 ml of chloroform, and 1.77 g of thionyl chloride were further fed dropwise to the resultant solution. The solution was then stirred for 1 hour at room temperature. After completed the reaction, the solution reacted was poured into ice-water and extracted with chloroform. The organic layer resulted was dried with anhydrous magnesium sulfate, and the solvent used was distillated under reduced pressure, thereby affording 3.2 g of 4-(3-phenylpropyloxy) benzylchloride.

0.43 g of imidazole were dissolved in 50 ml of acetonitrile, then 0.95 g of potassium carbonate were further added to the resultant solution. The solution was then further fed dropwise with 4-(3-phenylpropyloxy)benzylchloride obtained hereinabove and stirred for a night while subjecting the solution to reflux under heating.

The solution reacted was cooled to room temperature, then the solvent used was distillated under reduced pressure. Then solution was then added with water and extracted with ethyl acetate. The organic layer resulted was dried with anhydrous magnesium sulfate, and the solvent used was distillated under reduced pressure. The residue obtained was purified by using silica gel column chromatography, for which chloroform was used for the developer, thereby affording 0.85 g of the final objective compound with a melting point of 79–82° C.

EXAMPLE 6

Manufacturing of 1-[4-(4-phenylbutyloxy)benzyl]imidazole

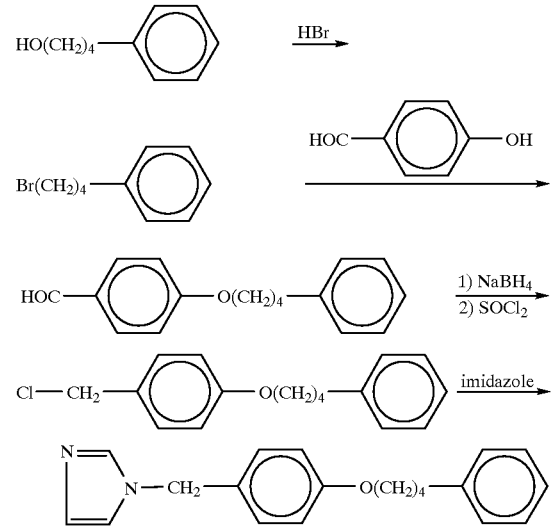

To 3.2 g of 4-phenyl-1-butanol, were added 1.0 g of concentrated sulfuric acid and 5.5 g of 47% aqueous solution of hydrobromic acid, and the resultant solution was stirred for 5 hours at 140–150° C. while applying heating. After completed the reaction, the solution was then poured into ice-water and extracted with ethyl acetate. The organic layer resulted was dried with anhydrous magnesium sulfate, and the solvent used was distillated under reduced pressure, thereby affording 2.7 g of 4-phenyl-1-bromobutane.

To 30 ml DMF solution wherein 1.73 g of 4-hydroxybenzaldehyde were dissolved, 0.57 g of 60% NaH were added while cooling the solution with ice, then the solution was stirred for 1 hour after elevating the temperature of the solution up to room temperature. Further, after cooling the solution with ice, 2.7 g of 4-phenyl-1-bromo butane were fed dropwise thereto, then the solution was further stirred for 1 hour at room temperature and subsequently for a night at 50–60° C. The solution reacted was poured into ice-water and extracted with ethyl acetate The organic layer resulted was dried with anhydrous magnesium sulfate, and the solvent used was removed by distillation under reduced pressure, thereby affording 3.5 g of 4-(4-phenylbutyloxy)benzaldehyde.

3.5 g of 4-(4-phenylbutyloxy)benzaldehyde obtained as hereinabove were dissolved in 30 ml of ethanol, and 0.26 g of sodium borohydride were further added to the resultant solution, and the solution was subsequently stirred for 1 hour at room temperature.

After completed the reaction, the solvent used was removed by distillation under reduced pressure, and the residue obtained was dissolved in a mixture of ethyl acetate and dilute hydrochloric acid. The ethyl acetate layer resulted was washed with dilute hydrochloric acid, dilute alkaline aqueous solution and water in series, and the organic layer resulted was dried with anhydrous magnesium sulfate, and the solvent used was removed by distillation under reduced pressure, thereby affording 2.9 g of 4-(4-phenylbutyloxy) benzyl alcohol.

2.9 g of 4-(4-phenylbutyloxy)benzyl alcohol were dissolved in 30 ml of chloroform, and 1.6 g of thionyl chloride were further fed dropwise to the resultant solution. The solution was then stirred for 1 hour at room temperature. After completed the reaction, the solution reacted was poured into ice-water and extracted with chloroform. The organic layer resulted was dried with anhydrous magnesium sulfate, and the solvent used was removed by distillation under reduced pressure, thereby affording 3.2 g of 4-(4-phenylbutyloxy)benzyl chloride.

0.87 g of imidazole were dissolved in 50 ml of acetonitrile, and 1.93 g of potassium carbonate were further added to the resultant solution. 3.2 g of 4-(4-phenylbutyloxy)benzyl chloride obtained as hereinabove were fed dropwise to the solution, and the solution was then stirred for a night while applying heating. After cooling the reacted solution to room temperature, the solvent used was removed by distillation under reduced pressure, and the residue obtained was added with water and extracted with ethyl acetate. The organic layer resulted was dried with anhydrous magnesium sulfate, and the solvent used was removed by distillation under reduced pressure. The residue obtained was purified by using silica gel column chromatography, for which a mixture of hexane and ethyl acetate (mixing ratio, 1:1) was used for the developer, thereby affording 1.95 g of the final objective compound with a melting point of 60–62° C.

EXAMPLE 7
Manufacturing of 1-[4-(2-phenoxyethyloxy)benzyl] imidazole

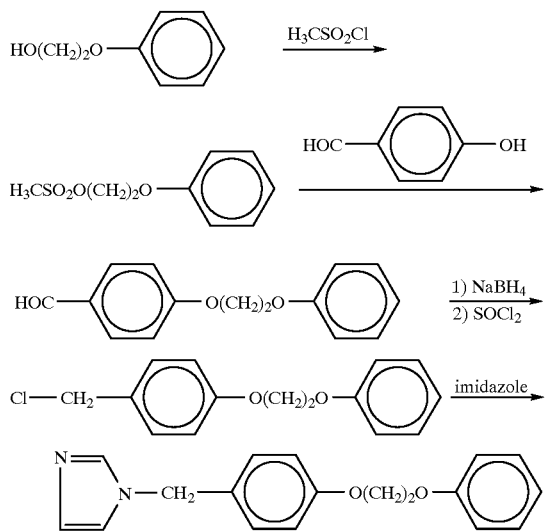

3.0 g of 2-phenoxy ethanol were dissolved in 30 ml of methylene chloride, and 3.3 g of triethylamine were further added to the resultant solution while cooling it with ice. The solution was then fed dropwise with 3.0 g of methane sulfonyl chloride and subsequently stirred for 1 hour at 0° C. and further for 2 hours at room temperature. After adding methylene chloride to the solution, the whole solution was then washed with water. The organic layer resulted was dried with anhydrous magnesium sulfate, and the solvent used was removed by distillation under reduced pressure, thereby affording 4.4 g of 2-phenoxyethyl-methane sulfonate.

1.19 g of 4-hydroxybenzaldehyde were dissolved in 30 ml of DMF, and 0.41 g of 60% NaH were further added to the resultant solution while cooling it with ice. The solution was then stirred for 1 hour after elevating the temperature of the solution up to room temperature. The solution was again cooled with ice, then added with 2.0 g of 2-phenoxyethyl-methane sulfonate, and stirred for 1 hour at room temperature and subsequently for a night at 50–60° C. The solution reacted was poured into ice-water and extracted with ethyl acetate, then the organic layer resulted was dried with anhydrous magnesium sulfate. The solvent used was then removed by distillation under reduced pressure, and the residue obtained was washed with a mixture of ether and hexane, thereby affording 1.45 g of 4-(2-phenoxyethyloxy) benzaldehyde.

1.45 g of 4-(2-phenoxyethyloxy)benzaldehyde obtained as described hereinabove were dissolved in 30 ml of ethanol, and 0.11 g of sodium borohydride were further added to the resultant solution, and the solution was then stirred for 1 hour at room temperature. After completed the reaction, the solvent used was removed by distillation under reduced pressure, and the residue obtained was dissolved in a mixture of ethyl acetate and dilute hydrochloric acid. The organic layer resulted was washed with dilute hydrochloric acid, dilute alkaline aqueous solution and water in series, and then dried with anhydrous magnesium sulfate, and the solvent used was removed by distillation under reduced pressure, thereby affording 1.1 g of 4-(2-phenoxyethyloxy) benzyl alcohol.

1.1 g of 4-(2-phenoxyethyloxy)benzyl alcohol obtained hereinabove were dissolved in 30 ml of chloroform. The resultant solution was then fed dropwise with 0.64 g of thionyl chloride and stirred for 1 hour at room temperature. After completed the reaction, the solution reacted was poured into ice-water and extracted with chloroform. The organic layer resulted was dried with anhydrous magnesium sulfate, and the solvent used was removed by distillation under reduced pressure, thereby affording 1.0 g of 4-(2-phenoxyethyloxy)benzyl chloride.

To 50 ml of acetonitrile solution containing 0.27 g of imidazole, were added 0.58 g of potassium carbonate and were then fed dropwise with 1.0 g of 4-(2-phenoxyethyloxy) benzyl chloride. The resultant solution was then stirred for a night while subjecting the solution to reflux under heating. The solution reacted was allowed to cooling up to room temperature, the solvent used was removed by distillation under reduced pressure, and the residue obtained was added with water and then extracted with ethyl acetate. The organic layer resulted was dried with anhydrous magnesium sulfate, and the solvent used was removed by distillation under reduced pressure. The residue obtained was purified by using silica gel column chromatography, for which chloroform was used for the developer, thereby affording 0.6 g of the final objective compound with a melting point of 159–160° C.

EXAMPLE 8
Manufacturing of 1-{4-[3-(4-tolyloxy)propyloxy]benzyl} imidazole

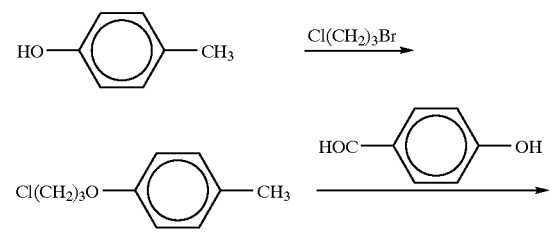

17

-continued

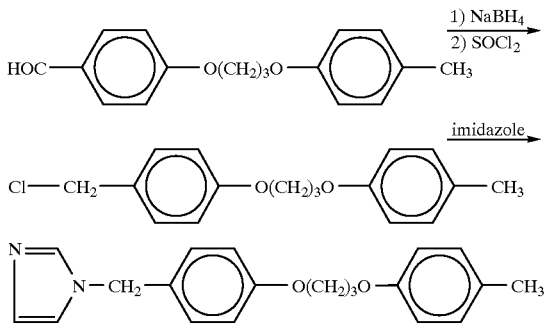

3.0g of p-cresol and 4.0 g of 3-bromo-1-chloro propane were placed into 20 ml of water and were subjected to reflux for 1 hour under heating, and whereto 20 ml of the aqueous solution of sodium hydroxide containing 1.2 g of sodium hydroxide were fed dropwise. After subjecting the resultant solution prepared as described hereinabove to reflux for another 2 hours, the solution reacted was poured into ice-water and extracted with ethyl acetate. The ethyl acetate layer resulted was washed with dilute aqueous alkaline solution and saturated saline solution in series, and the organic layer resulted was then dried with anhydrous magnesium sulfate, and the solvent used was removed by distillation under reduce pressure, thereby affording 3.6 g of 3-(4-tolyloxy)-1-chloro propane.

To 30 ml of DMF solution containing 1.45 g of 4-hydroxybenzaldehyde, were added 0.48 g of NaH while cooling the solution with ice, and the resultant solution was stirred for 1 hour following to elevating the temperature of the solution up to room temperature. The solution was again cooled with ice, then fed dropwise with 2.0 g of 1-(4-tolyloxy)-3-chloro propane and subsequently stirred for 1 hour at room temperature and further for a night at 50–60° C.

After completed the reaction, the solution reacted was poured into ice-water and extracted with ethyl acetate. The organic layer resulted was dried with anhydrous magnesium sulfate, and the solvent used was removed by distillation under reduced pressure, thereby affording 3.0 g of 4-[3-(4-tolyloxy)-propyloxy]-benzaldehyde.

3.0 g of 4-[3-(4-tolyloxy)propyloxy]benzaldehyde were dissolved in 30 ml of ethanol, and the resultant solution was then stirred for 1 hour at room temperature following to the addition of 0.21 g of sodium borohydride to the said solution. After completed the reaction, the solvent used was removed by distillation under reduced pressure, and the residue obtained was dissolved in a mixture of ethyl acetate and dilute hydrochloric acid. The ethyl acetate layer resulted was then washed with dilute hydrochloric acid, dilute aqueous alkaline solution and water in series. The organic layer resulted was dried with anhydrous magnesium sulfate, and the solvent used was removed by distillation under reduced pressure, thereby affording 1.67 g of 4-[3-(4-tolyloxypropyloxy]benzyl alcohol.

1.67 g of 4-[3-(4-tolyloxy)propyloxy]benzyl alcohol were dissolved in 30 ml of chloroform, and the resultant solution was then stirred for 1 hour at room temperature after conducting the dropping of 0.88 g of thionyl chloride into the solution. The solution reacted was then poured into ice-water and extracted with chloroform, and the organic layer resulted was dried with anhydrous magnesium sulfate, and the solvent used was removed by distillation under reduced pressure thereby affording 1.9 g of 4-[3-(4-tolyloxy) propyloxy]benzyl chloride.

18

To 50 ml of acetonitrile solution containing 0.49 g of imidazole, were added 1.08 g of potassium carbonate, and the resultant solution was then fed dropwise with 1.9 g of 4-[3-(4-tolyloxy)propyloxy]benzyl chloride. The solution was then stirred for a night while allowing it to reflux under heating. After completed the reaction, the solution reacted was cooled to room temperature, and the solvent used was removed by distillation under reduced pressure. The solution was then added with water and extracted with ethyl acetate. The organic layer resulted was dried with anhydrous magnesium sulfate, and the solvent used was removed by distillation under reduced pressure. The residue obtained was further purified by using silica gel column chromatography, for which chloroform was used for the developer, thereby affording 1.3 g of the objective compound with a melting point of 107–109° C.

EXAMPLE 9

Manufacturing of 1-[(4-octyloxy)benzyl]imidazole

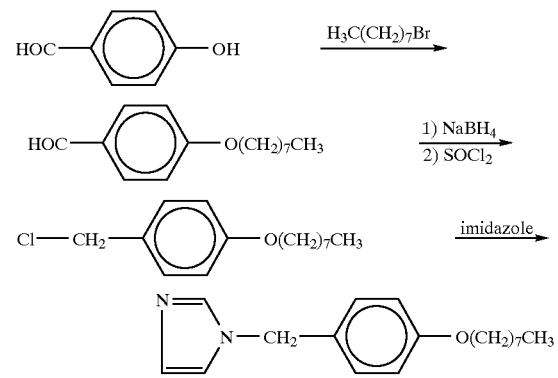

2.0 g of 4-hydroxybenzaldehyde were dissolved in 20 ml of DMF, and the resultant solution was further added with 0.66 g of 60% NaH while cooling with ice and then stirred for 1 hour after elevating the temperature of the solution up to room temperature. After cooling the solution again with ice, 2.9 g of n-octyl bromide were fed dropwise thereto, and the solution was then stirred for 1 hour at room temperature and further for a night at 50–60° C.

The solution reacted was poured into ice-water and then extracted with ethyl acetate. The organic layer resulted was dried with anhydrous magnesium sulfate, and the solvent used was removed by distillation under reduced pressure, thereby affording 3.55 g of 4-octyloxy benzaldehyde.

3.55 g of 4-octyloxy benzaldehyde were dissolved in 50 ml of ethanol, and the resultant solution was further added with 0.29 g of sodium borohydride and then stirred for 1 hour at room temperature. After completed the reaction, the solvent used was removed by distillation under reduced pressure, and the residue obtained was dissolved in a mixture of ethyl acetate and dilute hydrochloric acid The ethyl acetate layer resulted was then washed with dilute hydrochloric acid, dilute aqueous alkaline solution and water in series. The organic layer resulted was then dried with anhydrous magnesium sulfate, and the solvent used was removed by distillation under reduced pressure, thereby affording 2.5 g of 4-octyloxybenzyl alcohol.

2.5 g of 4-octyloxybenzyl alcohol were dissolved in 20 ml of chloroform, and the resultant solution was further fed dropwise with 1.48 g of thionyl chloride and then stirred for 1 hour at room temperature. The solution reacted was poured into ice-water and extracted with chloroform. The organic layer resulted was then dried with anhydrous magnesium sulfate, and the solvent used was removed by distillation under reduced pressure, thereby affording 2.2 g of 4-octyloxybenzyl chloride.

To 50 ml of acetonitrile solution containing 0.58 g of imidazole, were added 1.35 g of potassium carbonate, and the resultant solution was fed dropwise with 2.2 g of 4-octyloxybenzyl chloride and then subjected to reflux for a night under heating. After cooling the solution to room temperature, the solvent used was removed by distillation under reduced pressure. The solution was then added with water and further extracted with ethyl acetate. The organic layer resulted was dried with anhydrous magnesium sulfate, and the solvent used was removed by distillation under reduced pressure. The residue obtained was further purified by using silica gel column chromatography, for which chloroform was used for the developer, thereby affording 0.9 g of the objective compound with a refractive index of nD$^{23.4}$ 1.5162.

EXAMPLE 10

Manufacturing of 1-[4-(3-benzenesulfonylpropyloxy) benzyl]imidazole

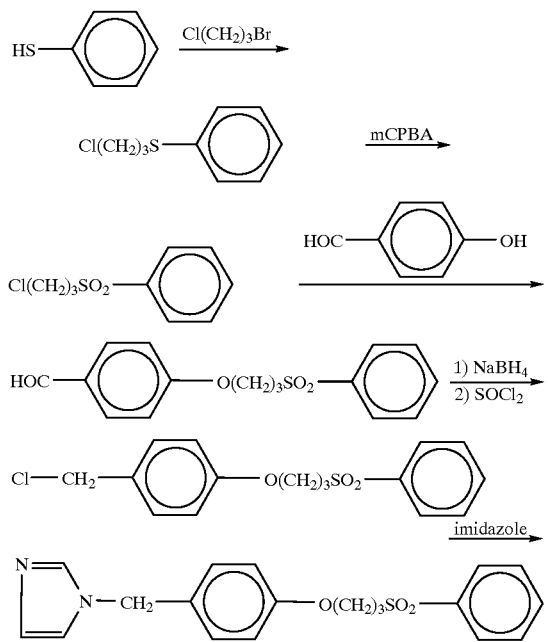

40 ml of an aqueous solution containing 6.0 g of thiophenol and 7.8 g of 3-bromo-1-chloropropane were subjected to reflux for 1 hour under heating. To the solution, 40 ml of aqueous solution of sodium hydroxide containing 2.4 g thereof were then fed dropwise. Then, the solution was further subjected to reflux for another 2 hours under heating, and the solution reacted was poured into ice-water and extracted with ethyl acetate. The ethyl acetate layer resulted was then washed with dilute aqueous alkaline solution and saturated saline solution in series, then dried with anhydrous magnesium sulfate. The solvent used was removed by distillation under reduced pressure, and the residue obtained was purified by using silica gel column chromatography, for which hexane was used for the developer, thereby affording 6.5 g of 1-chloro-3-phenylthio propane.

1.15 g of 1-chloro-3-phenylthio propane obtained as described hereinabove were dissolved in 30 ml of chloroform, and the resultant solution was further added with 1.2 g of m-chloro perbenzoic acid while cooling the solution with ice and stirred for 1 hour after elevating the temperature of the solution to room temperature. The solution was then again added with 1.2 g of m-chloro perbenzoic acid and stirred for another 2 hours. After completed the reaction, the solution was poured into ice-water and extracted with chloroform. The organic layer resulted was washed with aqueous solution of sodium hydroxide and then dried with anhydrous magnesium sulfate, and the solvent used was removed by distillation under reduced pressure, thereby affording 1.5 g of 1-chloro-3-benzenesulfonyl propane.

0.72 g of 4-hydroxybenzaldehyde were dissolved in 30 ml of DMF, and the resultant solution was further added with 0.3 g of 60% NaH and stirred for 1 hour after elevating the temperature of the solution to room temperature. The solution was then further fed dropwise with 1.5 g of 1-chloro-3-benzenesulfonyl propane while cooling the solution with ice, and was stirred for 1 hour at room temperature and further for a night at 50–60° C.

After completed the reaction, the solution reacted was poured into ice-water and extracted with ethyl acetate. The organic layer resulted was washed with aqueous solution of sodium hydroxide and then dried with anhydrous magnesium sulfate, and the solvent used was removed by distillation under reduced pressure, thereby affording 1.8 g of 4-(3-benzenesulfonylpropyloxy)benzaldehyde.

1.8 g of 4-(3-benzenesulfonylpropyloxy)benzaldehyde were dissolved in 30 ml of ethanol, and the resultant solution was further added with 0.11 g of sodium borohydride and then stirred for 1 hour at room temperature. After completed the reaction, the solvent used was removed by distillation under reduced pressure, and the residue obtained was dissolved in a mixture of ethyl acetate and dilute hydrochloric acid. The ethyl acetate layer resulted was then washed with dilute hydrochloric acid, aqueous solution of sodium hydroxide and water in series. The organic layer resulted was then dried with anhydrous magnesium sulfate, and the solvent used was removed by distillation under reduced pressure, thereby affording 1.5 g of 4-(3-benzenesulfonylpropyloxy)benzyl alcohol.

1.5 g of 4-(3-benzenesulfonylpropyloxy)benzyl alcohol were dissolved in 30 ml of chloroform, and the resultant solution was further fed dropwise with 0.7 g of thionyl chloride and then stirred for 1 hour at room temperature. After completed the reaction, the solution reacted was poured into ice-water and extracted with chloroform. The organic layer resulted was dried with anhydrous magnesium sulfate, and the solvent used was removed by distillation under reduced pressure, thereby affording 1.6 g of 4-(3-benzenesulfonylpropyloxy)benzyl chloride.

To 50 ml of acetonitrile solution containing 0.37 g of imidazole, were added 0.82 g of potassium carbonate and subsequently 1.6 g of 4-(3-benzenesulfonylpropyloxy) benzyl chloride, and the resultant solution was then subjected to reflux for a night under heating. After cooling the reacted solution to room temperature, the components having a low boiling point were removed by distillation under reduced pressure. The solution was then added with water and extracted with ethyl acetate. The organic layer resulted was dried with anhydrous magnesium sulfate, and the solvent used was removed by distillation under reduced pressure. The residue obtained was further purified by using silica gel column chromatography, for which chloroform was used for the developer, thereby affording 0.6 g of the objective compound with a melting point of 50–52° C.

EXAMPLE 11
Manufacturing of 1-[4-(3-phenylthiopropyloxy)benzyl]imidazole

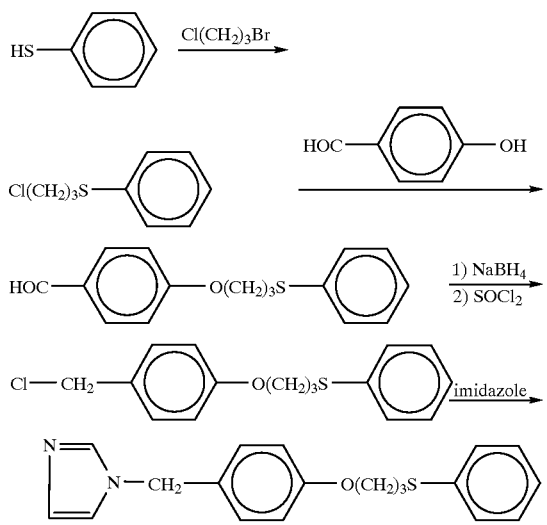

6.0 g of thiophenol and 7.8 g of 3-bromo-1-chloropropane were placed in 40 ml of water, and the resultant solution was subjected to reflux for 1 hour under heating. Then, 40 ml of an aqueous solution containing 2.4 g of sodium hydroxide were fed dropwise to the solution. The solution was then further subjected to reflux for another 2 hours under heating. The solution reacted was then poured into ice-water and extracted with ethyl acetate. The ethyl acetate layer resulted was then washed with dilute aqueous alkaline solution and saturated saline solution in series, and the organic layer resulted was dried with anhydrous magnesium sulfate. The solvent used was removed by distillation under reduced pressure, and the residue obtained was then purified by using silica gel column chromatography, for which hexane was used for the developer, thereby affording 6.5 g of 1-chloro-3-phenylthio propane.

0.69 g of 4-hydroxybenzaldehyde were dissolved in 30 ml of DMF, and the resultant solution was further added with 0.24 g of 60% NaH while cooling the solution with ice and then stirred for 1 hour after elevating the temperature of the solution to room temperature. Further, the solution was fed dropwise with 1.0 g of 1-chloro-3-phenylthio propane while cooling the solution with ice and then stirred for 1 hour at room temperature and further for a night at 50–60° C. After completed the reaction, the solution reacted was poured into ice-water and extracted with ethyl acetate. The organic layer resulted was then washed with aqueous solution of sodium hydroxide and dried with anhydrous magnesium sulfate, and the solvent used was removed by distillation under reduced pressure, thereby affording 1.2 g of 4-(3-phenylthiopropyloxy)-benzaldehyde.

1.2 g of 4-(3-phenylthiopropyloxy)benzaldehyde were dissolved in 30 ml of ethanol, and the resultant solution was further added with 0.08 g of sodium borohydride and then stirred for 1 hour at room temperature. After completed the reaction, the solvent used was removed by distillation under reduced pressure, and the residue obtained was dissolved in a mixture of ethyl acetate and dilute hydrochloric acid. The ethyl acetate layer resulted was then washed with dilute hydrochloric acid, aqueous solution of sodium hydroxide and water in series. The organic layer resulted was then dried with anhydrous magnesium sulfate, and the solvent used was removed by distillation under reduced pressure, thereby affording 0.65 g of 4-(3-phenylthiopropyloxy)benzyl alcohol.

0.65 g of 4-(3-phenylthiopropyloxy)benzyl alcohol were dissolved in 30 ml of chloroform, and the resultant solution was further fed dropwise with 0.34 g of thionyl chloride and then stirred for 1 hour at room temperature. The solution reacted was poured into ice-water and extracted with chloroform. The organic layer resulted was then dried with anhydrous magnesium sulfate, and the solvent used was removed by distillation under reduced pressure, thereby affording 0.8 g of 4-(37phenylthiopropyloxy)benzyl chloride.

To 50 ml of acetonitrile solution containing 0.2 g of imidazole, were added 0.45 g of potassium carbonate and subsequently 0.8 g of 4-(3-phenylthiopropyloxy)benzyl chloride, and the resultant solution was then subjected to reflux for a night under heating. After cooling the reacted solution to room temperature, the solvent used was removed by distillation under reduced pressure. The solution was then added with water and extracted with ethyl acetate. The organic layer resulted was dried with anhydrous magnesium sulfate, and the solvent used was removed by distillation under reduced pressure. The residue obtained was further purified by using silica gel column chromatography, for which chloroform was used for the developer, thereby affording 0.45 g of the objective compound with a melting point of 60.5–62° C.

EXAMPLE 12
Manufacturing of 1-[4-(3-benzenesulfonylpropyloxy)benzyl]imidazole hydrochloride

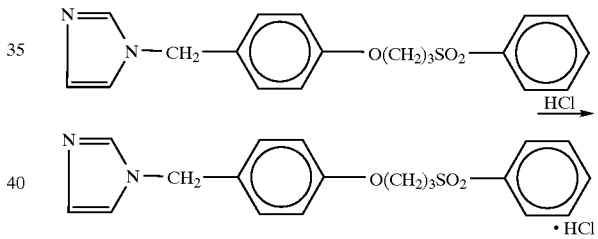

0.55 g of 1-[4-(3-benzenesulfonylpropyloxy)benzyl]imidazole were dissolved in a mixed solvent of ether and DME, and hydrogen chloride gas was blown into the resultant solution for 5 minutes. The crystals precipitated were separated by filtration, thereby affording 0.49 g of 1-[4-(3-benzenesulfonylpropyloxy)benzyl]imidazole hydrochloride with a melting point of 194–196° C.

The representative examples for the compounds according to the present invention including the compounds described in the examples above are presented in Tables 1 and 2, hereinbelow.

TABLE 2

| Compound No. | $R^1$ | X—$(CH_2)_m$—A | Physical Constant |
| --- | --- | --- | --- |
| 2-117 | H | O—$C_8H_{17}$ | $n_D^{23.4}$ 1.5162 |
| 2-118 | H | O—$C_9H_{19}$ | |
| 2-119 | H | O—$C_{10}H_{21}$ | |
| 2-120 | H | O—$C_{11}H_{23}$ | |
| 2-121 | H | SO—$C_8H_{17}$ | |

The compounds of the present invention are useful as an antihyperlipemic agent, an antithrombotic agent and therapeutic and preventive drugs for arteriosclerosis, and the compounds represented by the general formula [I] and the pharmaceutically-acceptable salts thereof can be administrated in either forms of without additional preparation or appropriate pharmaceutical preparations according to the pharmaceutically-acceptable modes of administration being adopted for such drugs having similar pharmaceutical effects. More particularly, the compounds of the present invention and the pharmaceutically-acceptable salts thereof can be administrated orally, pernasally, parenterally, locally, percutaneously and perrectally, and in any dosage forms in solid, semisolid, lyophilized powder or liquid, for examples, tablets, suppositories, pills, soft and hard capsules, powders, solutions, suspensions and aerosols, and preferably in unit dosage forms suitable for simple administration with an accurate dosage.

For the pharmaceutical preparations, pharmaceutical carriers and fillers can be contained together with the compound represented by the general formula [I] useful as the sole active principle or one of the active principles, however, it is possible to further add other active principles, other components for the pharmaceutical preparation, carriers and adjuvants.

In general, the pharmaceutically-acceptable preparations specified herein are composed of approximately from 1 to 99% by weight of one or more of either the compounds represented by the general formula [I] or the pharmaceutically-acceptable salts thereof and approximately from 99 to 1% by weight of appropriate pharmaceutical fillers, though those may vary depending upon the intended route of the administration.

Preferably, the pharmaceutical preparations are composed of approximately from 5 to 75% by weight of one or more of either the compounds represented by the general formula [I] or the pharmaceutically-acceptable salts thereof and appropriate pharmaceutical fillers for the rest.

The preferable route of the administration for the compounds of the present invention is oral administration, and for which simple and easy daily standard dosage determined basing on the seriousness of the diseases, namely hypercholesterolemia, hyperlipemia and arteriosclerosis, to be treated, can be adopted.

The preparation of orally administrative pharmaceutical preparations comprising one or more of either the compounds represented by the general formula [I] or the pharmaceutically-acceptable salts thereof, cab be made by optionally adding pharmaceutical fillers customarily used, such as mannitol, milk sugar, starch, gelatinized starch, magnesium stearate, saccharin sodium, talc, cellulose ether derivatives, glucose, gelatin, sucrose, citrates and propyl gallate.

The orally administrative pharmaceutical preparations described above can be prepared in dosage forms, such as solutions, suspensions, tablets, pills, capsules, powders and continuous release preparations. However, it is preferable to prepare the orally administrative pharmaceutical preparations of the compounds of the present invention into the dosage forms of capsules, wafer capsules or tablets. In these dosage forms, diluents, such as milk sugar, sucrose and calcium (II) phosphate, disintegrators, such as sodium chloscalmelose and the derivatives thereof, lubricants, such as magnesium stearate, binders, such as starch, acacia, poly(N-vinylpyrrolidone), gelatin and cellulose ether derivatives, may be combined.

The compounds represented by the general formula [I] and the pharmaceutically-acceptable salts thereof can be prepared to a dosage form of suppositories wherein the active principle in an amount of from approximately 0.5% to approximately 50% by weight were dispersed in a pharmaceutical carrier, such as polyoxyethylene glycol and polyethylene glycol (hereinafter referred to as PEG), more particularly PEG 1000 (96%) or PEG 4000 (4%), those which can dissolve gradually in the body.

The solutions administrative as drugs can be prepared by dissolving or suspending one or more of either the compounds represented by the general formula [I] in an amount of from approximately 0.5% to approximately 20% by weight or the pharmaceutically-acceptable salts thereof and optionally-selected pharmaceutical adjuvant in a carrier, such as water, saline solution, aqueous solution of dextrose, glycerol and ethanol, to thereby make them into a form of either solution or suspension.

To the pharmaceutical preparations according to the present invention, small amount of auxiliary agents, such as moistening agents or emulsifiers, pH buffers agents and antioxidants, for example, citric acid, sorbitan monolaurate, triethanol amine oleate, butylated hydroxy toluene, etc. may be added, if appropriate.

The dosage forms described above can be practically manufactured according to the methods customarily known, for example, the method reported in Remington's pharmaceutical Sciences, Vol.18, Mack publishing Company, Easton, Pa., 1990.

In any case, the pharmaceutical preparations to be dosed contain one or more of the compounds represented by the general formula [I] or the pharmaceutically-acceptable salts thereof in an amount of the dose therapeutically effective to remedy hypercholesterolemia, hyperlipemia and arteriosclerosis, if the said pharmaceutical preparations were administrated according to the teaching in the present invention.

The compounds represented by the general formula [I] and the pharmaceutically-acceptable salts thereof are generally administrated at their effective dose, which varies depending upon the conditions of the patient and the seriousness of the disease specific to hypercholesterolemia, hyperlipemia and arteriosclerosis to be treated, respectively. Normally, the therapeutically effective dosage per kg body weight per day of the compounds represented by the general formula [I] is in a range of from approximately 0.14 mg/kg/day to approximately 14.3 mg/kg/day, and preferably from approximately 0.7 mg/kg/day to approximately 10 mg/kg/day, and more preferably from approximately 1.4 mg/kg/day to approximately 7.2 mg/kg/day. For example, in case of the administration to a person of 70 kg in weight, the daily dosage range of the compounds represented by the general formula [I] or the pharmaceutically-acceptable salts thereof to the person is from approximately 10 mg/day to approximately 1.0 g/day, and preferably from approximately 50 mg/day to 700 mg/day, and more preferably from approximately 100 mg/day to approximately 500 mg/day.

Pharmacological Test Example 1

Inhibitory Effect on Biosynthesis of Cholesterol in Cell-free Biosystem (1) Preparation of Enzyme Reaction System The preparation of the enzymatic system for the biosynthesis of cholesterol in rats was carried out according to the method described in Biochimica et Biophysica Acta, Vol.486, pp 70–81, 1977.

More particularly, SD-strain female rats weighing from 110 to 130 kg were fed for 7 to 10 days with a diet containing 2% cholestyramine to enhance their biosynthetic activity of cholesterol. After killed the rats by means of depletion of blood in midnight, the livers thereof were removed and homogenized with a double volume of 0.1 M potassium phosphate buffer solution (pH 7.4) containing 15 mM nicotine amide and 2 mM magnesium chloride by using a loose fitting-type teflon homogenizer. The supernatant obtained by centrifuging the homogenate at 12,000×g for 30 min. was further centrifuged at 105,000×g for 90 min., thereby separating it to the microsome fraction and the supernatant fraction. The supernatant obtained were kept as the fraction resulting in the precipitation in 40–80% ammonium sulfate (hereinafter referred to as "soluble fraction"). Each of the soluble fraction and the microsome fraction were independently adjusted with 0.1 M potassium phosphate buffer solution (pH 7.4) to the volumes of 1 ml/g of liver and 1 ml/3 g of liver, respectively, and were kept and used in the subsequent tests as an enzyme solution for the mixing ratio of 16:1.

(2) Method for Measuring Cholesterol Biosynthesis Activity

Cholesterol biosynthesis activity was measured according to the method described in Biochimica Biophysica Acta, Vol.486, pp 70–81, 1977. 2 $\mu l$ dimethylsulfoxide solution of the test compound were added to a solution composed of 50 $\mu l$ of the enzyme solution prepared in (1) described above, 0.1 M potassium phosphate buffer solution (pH 7.4), 1 mM ATP, 5 mM glucose-1-phosphate, 6 mM glutathione, 6 mM magnesium chloride, 0.04 mM coenzyme A, 0.25 mM NAD, 0.25 mM NADP and 1 mM 2-$^{14}$C-sodium acetate (111 MBq./mmol), and the resultant solution was adjusted to the whole volume of 0.2 ml and then allowed to a reaction for 90 min. at 37° C. while shaking. The reaction was then stopped by adding 1 ml of 15% ethanol solution of potassium hydroxide, and the solution was then heated for 1 hour at 75° C. After extracted unsaponificated products with hexane from the solution, the solution was then condensed and dried to the hard state and subsequently dissolved in small volume of a mixture of chloroform and methanol (mixing ratio; 1:2). The resultant chloroform-methanol solution was spotted on a pre-coated silica gel TLC plate, then developed with a developer composed of benzene and ethyl acetate (mixing ratio; 9:1). The cholesterol spot was then taken out from the plate, and the radient activity of the spot was measured by using a liquid scintillation counter. Based on the radio-activity measured, mthe 50% inhibitory concentration ($IC_{50}$) of the compounds of the present invention were determined. The results are shown in Table 3.

On the other hand, after determining the position of $^{14}$C-squalene-2,3-epoxide on the TLC, which was produced due to the action of AMO 1618 (Calbiochem, USA), a squalene-2,3-oxidecyclase inhibitor, the spot containing squalene-2,3-epoxide cyclase was taken out and the radio-activity thereof was then determined by using a liquid scintillation counter. As shown in the Table 4, it was demonstrated that the compounds of the present invention inhibited the activity of squalene-2,3-oxide cyclase in the cholesterol biosynthesis cycle, since the amount of $^{14}$C-squalene-2,3-epoxide increased corresponding to the decrease in the synthesis of $^{14}$C-cholesterol.

TABLE 3

Inhibitory Effect on Cholesterol Biosynthesis

| Compound No. | 50% Inhibitory Concentration ($IC_{50}$, $\mu M$) |
|---|---|
| 1-17 | 1.5 |
| 1-20 | 0.7 |
| 1-24 | 2.6 |

TABLE 3-continued

Inhibitory Effect on Cholesterol Biosynthesis

| Compound No. | 50% Inhibitory Concentration ($IC_{50}$, $\mu M$) |
|---|---|
| 1-27 | 1.8 |
| 1-33 | 6.2 |
| 1-35 | 2.2 |
| 1-47 | 7.0 |
| 1-48 | 1.4 |
| 1-49 | 0.68 |
| 1-53 | 1.7 |
| 1-60 | 4.8 |
| 1-61 | 4.0 |
| 1-71 | 2.4 |
| 1-115 | 10 |
| 1-119 | 9.0 |
| 2-47 | 1.4 |
| 2-49 | 1.2 |
| 2-59 | 21 |
| 2-60 | 10 |
| 2-64 | 6.0 |
| 2-68 | <1.0 |
| 2-71 | <1.0 |
| 2-72 | 6.0 |
| 2-95 | 2.4 |
| 2-117 | 22 |
| AMO 1618 | 140 |

TABLE 4

Sterol Amount Synthesized

| Compound No. | Average of 6 results on Sterol Amount Synthesized (dpm/90min/Assay) | | |
|---|---|---|---|
| | Cholesterol | Squalene-2,3-epoxide | Total Amount Synthesized |
| Test 1 | | | |
| Control 1-17 | 15448 | 2125 | 85102 |
| 1 $\mu M$ | 15297 | 3238 | 72069 |
| 3 $\mu M$ | 8938 | 2102 | 82446 |
| 10 $\mu M$ | 6364 | 7382 | 79733 |
| 30 $\mu M$ | 3558 | 10914 | 95990 |
| 100 $\mu M$ | 1830 | 12736 | 77489 |
| Test 2 | | | |
| Control 2-47 | 9453 | 953 | 53622 |
| 1 $\mu M$ | 5289 | 221 | 53803 |
| 3 $\mu M$ | 6333 | 1280 | 56335 |
| 10 $\mu M$ | 4210 | 1836 | 72823 |
| 30 $\mu M$ | 3787 | 7126 | 63661 |

Pharmacological Test Example 2

In Vivo Inhibition Test on Cholesterol Biosynthesis

For this test, Crj:ICR-strain male mice aged 7–9 weeks were provided. The mice were fed with a diet containing 2% cholestyramine for 7 to 10 days under reversed lighting condition, namely the mice were placed in dark condition during 7:00 AM to 7:00 PM. Each of the test compounds was dissolved or suspended in either distilled water or 1% aqueous solution of poly(oxyethylene) curing castor oil and was orally administrated to the mice at a dose of 30 mg/kg at 10:30 AM, respectively. After 1 hour following to the administration of the test compound, the mice were intraperitoneally administrated with $^{14}$C-sodium acetate at a dose of 5 μCi/0.5 ml/mouse, respectively. After 2 hours, blood sampling was performed for each mouse from the abdominal aorta under anesthesia with ether and the blood sampled were placed into plastic test tubes being placed with blood separating agent beforehand to separate the serum, respectively. Each 0.5 ml of the serum was then added with 1 ml of 20% ethanol solution of potassium hydroxide and heated for 3 hours at 75° C. After extracting the unsponified substance with n-hexane, the serum was condensed to the dry hard state and dissolved in small amount of a mixed solution of chloroform and methanol (mixing ratio; 1:2). The resultant chloroform-methanol solution was then spotted on pre-coated silica gel TLC and developed with a mixed solution of benzene and ethyl acetate (mixing ratio; 9:1). The cholesterol spot was then taken out and the radio-activity thereof was measured by using a liquid scintillation counter. Based on the radio-activity measured, the inhibition rate on cholesterol biosynthesis were determined respectively for the compounds of the present invention. The results are shown in Table 5, hereinbelow.

TABLE 5

Inhibition Test on Cholesterol Biosynthesis in Mice (n = 5)

| Compound No. | $^{14}$C-Cholesterol, dpm/1 ml Serum | Inhibition Rate % |
|---|---|---|
| Control Group | 3783 | |
| 1-71 | 575 | 85 |
| Control Group | 5694 | |
| 2-64 | 460 | 92 |
| 2-71 | 73 | 99 |
| 2-72 | 3980 | 30 |

Pharmacological Test Example 3

Effect on Serum Lipid

For this test, Crj:ICR-strain male mice aged 7–9 weeks were provided. The mice were intravenously administrated with physiological saline solution of Triton WR-1339 through the tail vein at a dose of 350 mg/10 ml/kg at 10:00 AM to 11:00 AM and simultaneously subjected to a fast. At each times of 3, 6 and 9 hours after the administration of Triton WR-1339, the mice were individually received three times oral administrations of the test compound being dissolved or suspended in 1% aqueous solution of poly (oxyethylene) curing castor oil at a dose of 33.3 mg/kg (total dose administrated: 100 mg/kg). After 24 hours, blood sampling was performed for each mouse from the abdominal aorta under anesthesia with ether, and the collected blood were placed into plastic test tubes being placed with a blood separating agent beforehand, then after 30 min. or 1 hour, the blood sampled was centrifuged at 10,000 rpm to obtain the serum. Total cholesterol value, HDL cholesterol value and total triglyceride value in the serum were respectively measured by using the measuring kits and automatic biochemical analyser. The results are shown in Table 6, hereinbelow.

TABLE 6

Effect on Serum Lipid in Triton WR-1339-Induced Hyperlipemia Mice

| | % Change of Serum Lipid to Control Group (Average of 10 animals | | |
|---|---|---|---|
| Compound No. 100 mg/kg, po | Total Cholesterole | HDL Cholesterole | Total glyceride |
| 1-17 | −29 | 78 | −46 |
| 1-27 | −14 | 65 | −22 |
| 1-47 | −16 | 46 | −23 |
| 1-60 | −22 | 52 | −37 |
| 1-71 | −23 | 82 | −20 |
| 1-115 | −17 | 22 | −25 |
| 2-49 | −16 | 20 | −10 |
| 2-71 | −30 | 60 | −21 |
| 2-72 | −21 | 28 | −29 |
| Pravastatin | −16 | −8 | −28 |

Industrial Use

As described above, the present invention provides novel imidazole derivatives, which have excellent antihyperlipemic effect, therapeutic and preventive effect on arteriosclerosis and are proven for the safeness but causeing no side effect, and the advantageous methods for manufacturing the said imidazole derivatives in an industrial scale.

TABLE 1 n = 0:

| | Structural Formula |
|---|---|
| | 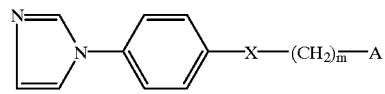 |
| Compound No. | X—(CH$_2$)$_m$—A | Physical Constant |
| 1-1 | 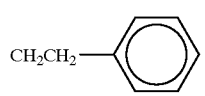 | [85–86] |
| 1-2 | 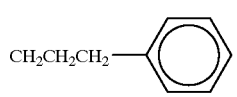 | |

TABLE 1-continued n = 0:

Structural Formula

[Imidazole-N-phenyl-X-(CH$_2$)$_m$-A structure]

| Compound No. | X—(CH$_2$)$_m$—A | Physical Constant |
|---|---|---|
| 1-3 | CH$_2$CH$_2$CH(CH$_3$)—C$_6$H$_5$ | |
| 1-4 | CH(CH$_3$)CH$_2$CH$_2$—C$_6$H$_5$ | |
| 1-5 | CH$_2$CH$_2$CH$_2$CH$_2$—C$_6$H$_5$ | [n$_D^{24.0}$ 1.5833] |
| 1-6 | CH$_2$CH$_2$CH$_2$CH(CH$_3$)—C$_6$H$_5$ | |
| 1-7 | CH(CH$_3$)CH$_2$CH$_2$CH$_2$—C$_6$H$_5$ | |
| 1-8 | CH$_2$CH$_2$CH$_2$CH$_2$CH$_2$—C$_6$H$_5$ | |
| 1-9 | CH$_2$CH$_2$CH$_2$CH$_2$CH(CH$_3$)—C$_6$H$_5$ | |
| 1-10 | CH(CH$_3$)CH$_2$CH$_2$CH$_2$CH$_2$—C$_6$H$_5$ | |
| 1-11 | CH$_2$CH$_2$CH$_2$CH$_2$CH$_2$CH$_2$—C$_6$H$_5$ | |
| 1-12 | CH$_2$CH$_2$CH$_2$CH$_2$CH$_2$CH(CH$_3$)—C$_6$H$_5$ | |
| 1-13 | CH(CH$_3$)CH$_2$CH$_2$CH$_2$CH$_2$CH$_2$—C$_6$H$_5$ | |

TABLE 1-continued n = 0:

Structural Formula

[imidazole-N-phenyl-X-(CH₂)ₘ-A structure]

| Compound No. | X—(CH₂)ₘ—A | Physical Constant |
|---|---|---|
| 1-14 | CH=NOCH₂CH₂CH₂CH₂—⟨phenyl⟩ | [65–67] |
| 1-15 | CH=NOCH₂CH₂CH₂—⟨phenyl⟩ | [62–63] |
| 1-16 | NHCH₂CH₂—⟨phenyl⟩ | [n_D^{23.0} 1.5998] |
| 1-17 | NHCH₂CH₂CH₂—⟨phenyl⟩ | [87–89.5] |
| 1-18 | NHCH₂CH₂CH₂—⟨phenyl⟩ ·HCl | [161–164] |
| 1-19 | NHCH₂CH₂CH(CH₃)—⟨phenyl⟩ | [n_D^{23.0} 1.6026] |
| 1-20 | NHCH₂CH₂CH₂CH₂—⟨phenyl⟩ | [n_D^{24.0} 1.6160] |
| 1-21 | NHCH₂CH₂CH₂CH(CH₃)—⟨phenyl⟩ | |
| 1-22 | NHCH₂CH₂CH₂CH₂CH₂—⟨phenyl⟩ | |
| 1-23 | NHCH₂CH₂CH₂CH₂CH(CH₃)—⟨phenyl⟩ | |
| 1-24 | NHCH₂CH₂CH₂CH₂CH₂CH₂—⟨phenyl⟩ | [n_D^{24.0} 1.6018] |
| 1-25 | NHCH₂CH₂CH₂CH₂CH₂CH(CH₃)—⟨phenyl⟩ | |

TABLE 1-continued n = 0:

Structural Formula

[Imidazolyl-phenyl-X-(CH$_2$)$_m$-A]

| Compound No. | X—(CH$_2$)$_m$—A | Physical Constant |
|---|---|---|
| 1-26 | N(CH$_3$)—CH$_2$CH$_2$—C$_6$H$_5$ | |
| 1-27 | N(CH$_3$)—CH$_2$CH$_2$CH$_2$—C$_6$H$_5$ | [78–80] |
| 1-28 | N(CH$_3$)—CH$_2$CH$_2$CH$_2$CH$_2$—C$_6$H$_5$ | |
| 1-29 | N(CH$_3$)—CH$_2$CH$_2$CH$_2$CH$_2$CH$_2$—C$_6$H$_5$ | |
| 1-30 | N(CH$_3$)—CH$_2$CH$_2$CH$_2$CH$_2$CH$_2$CH$_2$—C$_6$H$_5$ | |
| 1-31 | NHCH$_2$O—C$_6$H$_5$ | |
| 1-32 | NHCH$_2$CH$_2$O—C$_6$H$_5$ | [109–111] |
| 1-33 | NHCH$_2$CH$_2$CH$_2$O—C$_6$H$_5$ | [92–93] |
| 1-34 | NHCH$_2$CH$_2$CH$_2$O—C$_6$H$_5$ · HCl | [113–115] |
| 1-35 | NHCH$_2$CH$_2$CH$_2$CH$_2$O—C$_6$H$_5$ | [122–124] |
| 1-36 | NHCH$_2$CH$_2$CH$_2$CH$_2$CH$_2$O—C$_6$H$_5$ | [n$_D^{27.6}$ 1.6055] |
| 1-37 | NHCH$_2$CH$_2$CH$_2$CH$_2$CH$_2$CH$_2$O—C$_6$H$_5$ | [109–111] |

TABLE 1-continued n = 0:

Structural Formula:

[imidazole]-N-[phenyl]-X-(CH$_2$)$_m$-A

| Compound No. | X—(CH$_2$)$_m$—A | Physical Constant |
|---|---|---|
| 1-38 | NHCH$_2$CH$_2$CH$_2$S—[phenyl] | [63–65] |
| 1-39 | NHCH$_2$CH$_2$CH$_2$NH—[phenyl] | [63.2–66.0] |
| 1-40 | N(CH$_3$)—CH$_2$O—[phenyl] | |
| 1-41 | N(CH$_3$)—CH$_2$CH$_2$O—[phenyl] | |
| 1-42 | N(CH$_3$)—CH$_2$CH$_2$CH$_2$O—[phenyl] | |
| 1-43 | N(CH$_3$)—CH$_2$CH$_2$CH$_2$CH$_2$O—[phenyl] | |
| 1-44 | N(CH$_3$)—CH$_2$CH$_2$CH$_2$CH$_2$CH$_2$O—[phenyl] | |
| 1-45 | N(CH$_3$)—CH$_2$CH$_2$CH$_2$CH$_2$CH$_2$CH$_2$O—[phenyl] | |
| 1-46 | OCH$_2$CH$_2$—[phenyl] | [96–97] |
| 1-47 | OCH$_2$CH$_2$CH$_2$—[phenyl] | [72–75] |
| 1-48 | OCH$_2$CH$_2$CH(CH$_3$)—[phenyl] | [n$_D^{26.0}$ 1.5850] |

TABLE 1-continued n = 0:

Structural Formula

[imidazolyl-phenyl-X-(CH$_2$)$_m$-A structure]

| Compound No. | X—(CH$_2$)$_m$—A | Physical Constant |
|---|---|---|
| 1-49 | OCH$_2$CH$_2$CH$_2$—Ph | [55–56] |
| 1-50 | OCH$_2$CH$_2$CH$_2$CH(CH$_3$)—Ph | |
| 1-51 | OCH$_2$CH$_2$CH$_2$CH$_2$CH$_2$—Ph | |
| 1-52 | OCH$_2$CH$_2$CH$_2$CH$_2$CH(CH$_3$)—Ph | |
| 1-53 | OCH$_2$CH$_2$CH$_2$CH$_2$CH$_2$CH$_2$—Ph | [53–54] |
| 1-54 | OCH$_2$CH$_2$CH$_2$CH$_2$CH$_2$CH(CH$_3$)—Ph | |
| 1-55 | S(=O)(CH$_2$)$_4$—Ph | [$n_D^{28.0}$ 1.6094] |
| 1-56 | OCH$_2$CH$_2$CH$_2$—Ph · HCl | [157–158] |
| 1-57 | SCH$_2$CH$_2$CH$_2$CH$_2$—Ph | [$n_D^{24.0}$ 1.6459] |
| 1-58 | OCH$_2$O—Ph | |
| 1-59 | OCH$_2$CH$_2$O—Ph | [138–140] |
| 1-60 | OCH$_2$CH$_2$CH$_2$O—Ph | [75–76] |

TABLE 1-continued n = 0:

Structural Formula

[imidazole-N-phenyl-X-(CH$_2$)$_m$-A structure]

| Compound No. | X—(CH$_2$)$_m$—A | Physical Constant |
|---|---|---|
| 1-61 | OCH$_2$CH$_2$CH$_2$CH$_2$O—[phenyl] | [92–94] |
| 1-62 | OCH$_2$CH$_2$CH$_2$CH$_2$CH$_2$O—[phenyl] | [39–41] |
| 1-63 | OCH$_2$CH$_2$CH$_2$CH$_2$CH$_2$CH$_2$O—[phenyl] | [78–80] |
| 1-64 | OCH$_2$CH$_2$CH$_2$S—[phenyl] | [62–64] |
| 1-65 | OCH$_2$CH$_2$CH$_2$S—[phenyl] ·HCl | [138–140] |
| 1-66 | OCH$_2$CH$_2$CH$_2$NH—[phenyl] | [103–104] |
| 1-67 | OCH$_2$CH$_2$SO$_2$—[phenyl] | [138–139] |
| 1-68 | OCH$_2$CH$_2$CH$_2$SO$_2$—[phenyl] | [136–139] |
| 1-69 | OCH$_2$CH$_2$CH$_2$SO$_2$—[phenyl] | [128–129] |
| 1-70 | OCH$_2$CH$_2$CH$_2$CH$_2$CH$_2$CH$_2$SO$_2$—[phenyl] | [105–106] |
| 1-71 | OCH$_2$CH$_2$CH$_2$SO$_2$—[phenyl] ·HCl | [194–196] |
| 1-72 | OCH$_2$CH$_2$CH$_2$NHSO$_2$—[phenyl] | [135–137] |

TABLE 1-continued n = 0:

Structural Formula

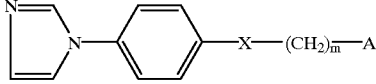

| Compound No. | X—(CH$_2$)$_m$—A | Physical Constant |
|---|---|---|
| 1-73 | 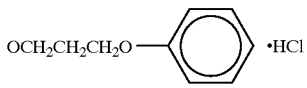 OCH$_2$CH$_2$CH$_2$O—⟨phenyl⟩ ·HCl | [123–126] |
| 1-74 | CH$_2$CH$_2$CH$_2$O—⟨phenyl⟩ | |
| 1-75 | CHCH$_2$CH$_2$O—⟨phenyl⟩<br>\|<br>CH$_3$ | |
| 1-76 | CH$_2$CH$_2$CH$_2$CH$_2$O—⟨phenyl⟩ | |
| 1-77 | CHCH$_2$CH$_2$CH$_2$O—⟨phenyl⟩<br>\|<br>CH$_3$ | |
| 1-78 | CH$_2$CH$_2$CH$_2$CH$_2$CH$_2$O—⟨phenyl⟩ | |
| 1-79 | CHCH$_2$CH$_2$CH$_2$CH$_2$O—⟨phenyl⟩<br>\|<br>CH$_3$ | |
| 1-80 | CH$_2$CH$_2$CH$_2$CH$_2$CH$_2$CH$_2$O—⟨phenyl⟩ | |
| 1-81 | CHCH$_2$CH$_2$CH$_2$CH$_2$CH$_2$O—⟨phenyl⟩<br>\|<br>CH$_3$ | |
| 1-82 | NH—CH$_2$CH$_2$O—⟨phenyl-m-CH$_3$⟩ | [88.5–90] |
| 1-83 | NH—CH$_2$CH$_2$O—⟨phenyl-p-CH$_3$⟩ | [95–97] |

TABLE 1-continued n = 0:

Structural Formula imidazol-1-yl—C6H4—X—(CH2)m—A

| Compound No. | X—(CH2)m—A | Physical Constant |
|---|---|---|
| 1-84 | NH—CH2CH2O—(3-Bu^t-C6H4) | [54–55] |
| 1-85 | NH—CH2CH2O—(4-Bu^t-C6H4) | [72–74] |
| 1-86 | NH—CH2CH2O—(2-Cl-C6H4) | [82–84] |
| 1-87 | NH—CH2CH2O—(4-Cl-C6H4) | [145–148] |
| 1-88 | NH—CH2CH2CH2O—(4-CH3-C6H4) | [119–121] |
| 1-89 | NH—CH2CH2CH2O—(3-Bu^t-C6H4) | [67–69] |
| 1-90 | NH—CH2CH2CH2O—(4-Bu^t-C6H4) | [amorphous] |
| 1-91 | NH—CH2CH2CH2CH2O—(3-Bu^t-C6H4) | [106–108] |
| 1-92 | NH—CH2CH2CH2CH2O—(4-Bu^t-C6H4) | [79–81] |
| 1-93 | O—CH2CH2—(4-Bu^t-C6H4) | [$n_D^{26.0}$ 1.5682] |

TABLE 1-continued n = 0:

Structural Formula

[imidazolyl-phenyl]–X–(CH$_2$)$_m$–A

| Compound No. | X—(CH$_2$)$_m$—A | Physical Constant |
|---|---|---|
| 1-94 | O—CH$_2$CH$_2$O—(2,6-dichlorophenyl) | [96–97] |
| 1-95 | O—CH$_2$CH$_2$CH$_2$O—(4-CH$_3$-phenyl) | [87–89] |
| 1-96 | O—CH$_2$CH$_2$CH$_2$O—(2-Pr$^i$-phenyl) | [n$_D^{26.2}$ 1.5757] |
| 1-97 | O—CH$_2$CH$_2$CH$_2$O—(4-Cl-phenyl) | [78–80] |
| 1-98 | O—CH$_2$CH$_2$CH$_2$O—(4-OCH$_3$-phenyl) | [66–67] |
| 1-99 | O—CH$_2$CH$_2$CH$_2$O—(2-Bu$^t$-phenyl) | [43–44] |
| 1-100 | O—CH$_2$CH$_2$CH$_2$O—(4-Bu$^t$-phenyl) | [34–35] |
| 1-101 | O—CH$_2$CH$_2$CH$_2$CH$_2$O—(2-Bu$^t$-phenyl) | [95–97] |
| 1-102 | O—CH$_2$CH$_2$CH$_2$CH$_2$O—(4-Bu$^t$-phenyl) | [118–120] |
| 1-103 | NH—CH$_2$CH$_2$O—(4-cyclohexyl-phenyl) | [129–131] |

TABLE 1-continued n = 0:

Structural Formula

[Imidazole-N-phenyl-X-(CH₂)ₘ-A structure]

| Compound No. | X—(CH₂)ₘ—A | Physical Constant |
|---|---|---|
| 1-104 | O—CH₂CH₂CH₂SO₂—[phenyl]—COOCH₃ | |
| 1-105 | O—CH₂CH₂CH₂SO₂—[phenyl]—COOH | |
| 1-106 | CH₂CH₂O—[2,4,6-trichlorophenyl] | |
| 1-107 | CH₂CH₂CH₂O—[3-chloro-4-methylphenyl] | |
| 1-108 | $C_8H_{17}$ | |
| 1-109 | $C_9H_{19}$ | |
| 1-110 | $C_{10}H_{21}$ | |
| 1-111 | $C_{11}H_{23}$ | |
| 1-112 | $C_{12}H_{25}$ | |
| 1-113 | NH—$C_8H_{17}$ | [53–55] |
| 1-114 | NH—$C_9H_{19}$ | |
| 1-115 | NH—$C_{10}H_{21}$ | [68–71] |
| 1-116 | H—$C_{11}H_{23}$ | |
| 1-117 | O—$C_8H_{17}$ | [23–27] |
| 1-118 | O—$C_9H_{19}$ | |
| 1-119 | O—$C_{10}H_{21}$ | |
| 1-120 | O—$C_{11}H_{23}$ | |
| 1-121 | SO—$C_8H_{17}$ | [$n_D^{25.5}$ 1.5670] |

TABLE 2 n = 1:

Structural Formula

[Imidazole-N-CH(R¹)-phenyl-X-(CH₂)ₘ-A structure]

| Compound No. | R¹ | X—(CH₂)ₘ—A | Physical Constant |
|---|---|---|---|
| 2-1 | H | CH₂CH₂—[phenyl] | |

TABLE 2-continued
n = 1:
Structural Formula
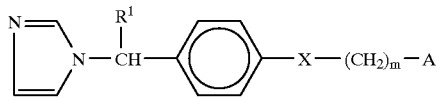
| Compound No. | R₁ | X—(CH₂)ₘ—A | Physical Constant |
|---|---|---|---|
| 2-2 | $CH_3$ | $CH_2CH_2CH_2$—Ph | |
| 2-3 | $C_2H_5$ | $CH_2CH_2CH(CH_3)$—Ph | |
| 2-4 | H | $CH(CH_3)CH_2CH_2$—Ph | |
| 2-5 | $CH_3$ | $CH_2CH_2CH_2CH_2$—Ph | |
| 2-6 | $C_2H_5$ | $CH_2CH_2CH_2CH(CH_3)$—Ph | |
| 2-7 | H | $CH(CH_3)CH_2CH_2CH_2$—Ph | |
| 2-8 | $CH_3$ | $CH_2CH_2CH_2CH_2CH_2$—Ph | |
| 2-9 | $C_2H_5$ | $CH_2CH_2CH_2CH_2CH(CH_3)$—Ph | |
| 2-10 | H | $CH(CH_3)CH_2CH_2CH_2CH_2$—Ph | |
| 2-11 | H | $CH_2CH_2CH_2CH_2CH_2CH_2$—Ph | |

TABLE 2-continued
n = 1:
Structural Formula
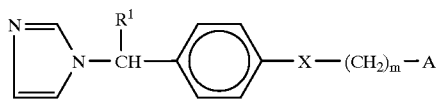
| Compound No. | R₁ | X—(CH₂)ₘ—A | Physical Constant |
|---|---|---|---|
| 2-12 | H | CH₂CH₂CH₂CH₂CH₂CH(CH₃)—C₆H₅ | |
| 2-13 | H | CH(CH₃)CH₂CH₂CH₂CH₂CH₂—C₆H₅ | |
| 2-14 | H | CH=NOCH₂CH₂CH₂—C₆H₅ | |
| 2-15 | H | CH=NOCH₂CH₂—C₆H₅ | |
| 2-16 | H | NHCH₂CH₂—C₆H₅ | |
| 2-17 | H | NHCH₂CH₂CH₂—C₆H₅ | |
| 2-18 | H | NHCH₂CH₂CH₂—C₆H₅ · HCl | |
| 2-19 | H | NHCH₂CH₂CH(CH₃)—C₆H₅ | |
| 2-20 | H | NHCH₂CH₂CH₂CH₂—C₆H₅ | |
| 2-21 | H | NHCH₂CH₂CH₂CH(CH₃)—C₆H₅ | |
| 2-22 | H | NHCH₂CH₂CH₂CH₂CH₂—C₆H₅ | |

TABLE 2-continued n = 1:

Structural Formula

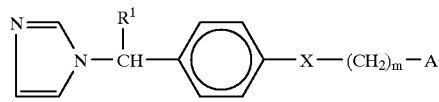

| Compound No. | R¹ | X—(CH$_2$)$_m$—A | Physical Constant |
|---|---|---|---|
| 2-23 | H | NHCH$_2$CH$_2$CH$_2$CH$_2$CH(CH$_3$)—C$_6$H$_5$ | |
| 2-24 | H | NHCH$_2$CH$_2$CH$_2$CH$_2$CH$_2$CH$_2$—C$_6$H$_5$ | |
| 2-25 | H | NHCH$_2$CH$_2$CH$_2$CH$_2$CH$_2$CH(CH$_3$)—C$_6$H$_5$ | |
| 2-26 | H | N(CH$_3$)—CH$_2$CH$_2$—C$_6$H$_5$ | |
| 2-27 | H | N(CH$_3$)—CH$_2$CH$_2$CH$_2$—C$_6$H$_5$ | |
| 2-28 | H | N(CH$_3$)—CH$_2$CH$_2$CH$_2$CH$_2$—C$_6$H$_5$ | |
| 2-29 | H | N(CH$_3$)—CH$_2$CH$_2$CH$_2$CH$_2$CH$_2$—C$_6$H$_5$ | |
| 2-30 | H | N(CH$_3$)—CH$_2$CH$_2$CH$_2$CH$_2$CH$_2$CH$_2$—C$_6$H$_5$ | |
| 2-31 | H | NHCH$_2$O—C$_6$H$_5$ | |
| 2-32 | H | NHCH$_2$CH$_2$O—C$_6$H$_5$ | |
| 2-33 | H | NHCH$_2$CH$_2$CH$_2$O—C$_6$H$_5$ | |

TABLE 2-continued n = 1:

Structural Formula

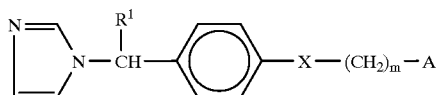

| Compound No. | R¹ | X—(CH$_2$)$_m$—A | Physical Constant |
|---|---|---|---|
| 2-34 | H | NHCH$_2$CH$_2$CH$_2$O—⟨phenyl⟩ ·HCl | |
| 2-35 | H | NHCH$_2$CH$_2$CH$_2$CH$_2$O—⟨phenyl⟩ | |
| 2-36 | H | NHCH$_2$CH$_2$CH$_2$CH$_2$CH$_2$O—⟨phenyl⟩ | |
| 2-37 | H | NHCH$_2$CH$_2$CH$_2$CH$_2$CH$_2$CH$_2$O—⟨phenyl⟩ | |
| 2-38 | H | NHCH$_2$CH$_2$CH$_2$S—⟨phenyl⟩ | |
| 2-39 | H | NHCH$_2$CH$_2$CH$_2$NH—⟨phenyl⟩ | |
| 2-40 | H | N(CH$_3$)—CH$_2$O—⟨phenyl⟩ | |
| 2-41 | H | N(CH$_3$)—CH$_2$CH$_2$O—⟨phenyl⟩ | |
| 2-42 | H | N(CH$_3$)—CH$_2$CH$_2$CH$_2$O—⟨phenyl⟩ | |
| 2-43 | H | N(CH$_3$)—CH$_2$CH$_2$CH$_2$CH$_2$O—⟨phenyl⟩ | |
| 2-44 | H | N(CH$_3$)—CH$_2$CH$_2$CH$_2$CH$_2$CH$_2$O—⟨phenyl⟩ | |

TABLE 2-continued
n = 1:
Structural Formula
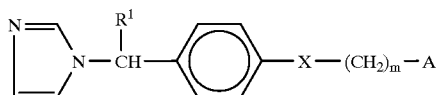
| Compound No. | R¹ | X—(CH₂)ₘ—A | Physical Constant |
|---|---|---|---|
| 2-45 | H | N(CH₃)—CH₂CH₂CH₂CH₂CH₂O—C₆H₅ | |
| 2-46 | H | OCH₂CH₂—C₆H₅ | |
| 2-47 | H | OCH₂CH₂CH₂—C₆H₅ | [79–82] |
| 2-48 | H | OCH₂CH₂CH(CH₃)—C₆H₅ | |
| 2-49 | H | OCH₂CH₂CH₂CH₂—C₆H₅ | [60–62] |
| 2-50 | H | OCH₂CH₂CH₂CH(CH₃)—C₆H₅ | |
| 2-51 | H | OCH₂CH₂CH₂CH₂CH₂—C₆H₅ | |
| 2-52 | H | OCH₂CH₂CH₂CH₂CH(CH₃)—C₆H₅ | |
| 2-53 | H | OCH₂CH₂CH₂CH₂CH₂CH₂—C₆H₅ | |
| 2-54 | H | OCH₂CH₂CH₂CH₂CH₂CH(CH₃)—C₆H₅ | |
| 2-55 | H | S(=O)(CH₂)₄—C₆H₅ | |

TABLE 2-continued n = 1:

Structural Formula

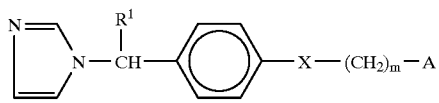

| Compound No. | R$^1$ | X—(CH$_2$)$_m$—A | Physical Constant |
|---|---|---|---|
| 2-56 | H | OCH$_2$CH$_2$CH$_2$—⟨phenyl⟩ ·HCl | |
| 2-57 | H | SCH$_2$CH$_2$CH$_2$CH$_2$—⟨phenyl⟩ | |
| 2-58 | H | OCH$_2$O—⟨phenyl⟩ | |
| 2-59 | H | OCH$_2$CH$_2$O—⟨phenyl⟩ | [159–160] |
| 2-60 | H | OCH$_2$CH$_2$CH$_2$O—⟨phenyl⟩ | [69–70.5] |
| 2-61 | H | OCH$_2$CH$_2$CH$_2$CH$_2$O—⟨phenyl⟩ | |
| 2-62 | H | OCH$_2$CH$_2$CH$_2$CH$_2$CH$_2$O—⟨phenyl⟩ | |
| 2-63 | H | OCH$_2$CH$_2$CH$_2$CH$_2$CH$_2$CH$_2$O—⟨phenyl⟩ | |
| 2-64 | H | OCH$_2$CH$_2$CH$_2$S—⟨phenyl⟩ | [60.5–62] |
| 2-65 | H | OCH$_2$CH$_2$CH$_2$S—⟨phenyl⟩ ·HCl | |
| 2-66 | H | OCH$_2$CH$_2$CH$_2$NH—⟨phenyl⟩ | |
| 2-67 | H | OCH$_2$CH$_2$SO$_2$—⟨phenyl⟩ | [130–131] |

TABLE 2-continued n = 1:

Structural Formula

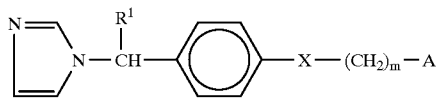

| Compound No. | R¹ | X—(CH$_2$)$_m$—A | Physical Constant |
|---|---|---|---|
| 2-68 | H | OCH$_2$CH$_2$CH$_2$SO$_2$—⌬ | [50–52] |
| 2-69 | H | OCH$_2$CH$_2$CH$_2$CH$_2$SO$_2$—⌬ | [87–88] |
| 2-70 | H | OCH$_2$CH$_2$CH$_2$CH$_2$CH$_2$CH$_2$SO$_2$—⌬ | [88–89] |
| 2-71 | H | OCH$_2$CH$_2$CH$_2$SO$_2$—⌬ ·HCl | [112–114] |
| 2-72 | H | OCH$_2$CH$_2$CH$_2$O—⌬ ·HCl | [128–131] |
| 2-73 | H | CH$_2$CH$_2$O—⌬ | |
| 2-74 | H | CH$_2$CH$_2$CH$_2$O—⌬ | |
| 2-75 | H | CHCH$_2$CH$_2$O—⌬<br>  \|<br>  CH$_3$ | |
| 2-76 | H | CH$_2$CH$_2$CH$_2$CH$_2$O—⌬ | |
| 2-77 | H | CHCH$_2$CH$_2$CH$_2$O—⌬<br>  \|<br>  CH$_3$ | |
| 2-78 | H | CH$_2$CH$_2$CH$_2$CH$_2$CH$_2$O—⌬ | |
| 2-79 | H | CHCH$_2$CH$_2$CH$_2$CH$_2$O—⌬<br>  \|<br>  CH$_3$ | |

TABLE 2-continued n = 1:

Structural Formula

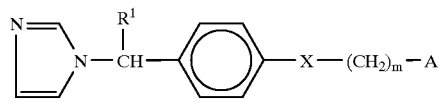

| Compound No. | R¹ | X—(CH$_2$)$_m$—A | Physical Constant |
|---|---|---|---|
| 2-80 | H | CH$_2$CH$_2$CH$_2$CH$_2$CH$_2$CH$_2$O—C$_6$H$_5$ | |
| 2-81 | H | CHCH$_2$CH$_2$CH$_2$CH$_2$O—C$_6$H$_5$, with CH$_3$ branch | |
| 2-82 | H | NH—CH$_2$CH$_2$O—(2-CH$_3$-C$_6$H$_4$) | |
| 2-83 | H | NH—CH$_2$CH$_2$O—(4-CH$_3$-C$_6$H$_4$) | |
| 2-84 | H | NH—CH$_2$CH$_2$O—(2-Bu$^t$-C$_6$H$_4$) | |
| 2-85 | H | NH—CH$_2$CH$_2$O—(4-Bu$^t$-C$_6$H$_4$) | |
| 2-86 | H | NH—CH$_2$CH$_2$O—(2-Cl-C$_6$H$_4$) | |
| 2-87 | H | NH—CH$_2$CH$_2$O—(4-Cl-C$_6$H$_4$) | |
| 2-88 | H | NH—CH$_2$CH$_2$CH$_2$O—(4-CH$_3$-C$_6$H$_4$) | |
| 2-89 | H | NH—CH$_2$CH$_2$CH$_2$O—(2-Bu$^t$-C$_6$H$_4$) | |

TABLE 2-continued n = 1:

Structural Formula

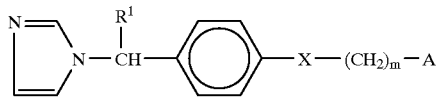

| Compound No. | R$^1$ | X—(CH$_2$)$_m$—A | Physical Constant |
|---|---|---|---|
| 2-90 | H | NH—CH$_2$CH$_2$CH$_2$O—⟨C$_6$H$_4$⟩—Bu$^t$ | |
| 2-91 | H | NH—CH$_2$CH$_2$CH$_2$CH$_2$O—⟨C$_6$H$_4$⟩(Bu$^t$ at meta) | |
| 2-92 | H | NH—CH$_2$CH$_2$CH$_2$CH$_2$O—⟨C$_6$H$_4$⟩—Bu$^t$ | |
| 2-93 | H | O—CH$_2$CH$_2$—⟨C$_6$H$_4$⟩—Bu$^t$ | |
| 2-94 | H | O—CH$_2$CH$_2$O—⟨C$_6$H$_3$⟩(Cl, Cl at 2,6) | |
| 2-95 | H | O—CH$_2$CH$_2$CH$_2$O—⟨C$_6$H$_4$⟩—CH$_3$ | [107–109] |
| 2-96 | H | O—CH$_2$CH$_2$CH$_2$O—⟨C$_6$H$_4$⟩(Pr$^i$ at meta) | |
| 2-97 | H | O—CH$_2$CH$_2$CH$_2$O—⟨C$_6$H$_4$⟩—Cl | |
| 2-98 | H | O—CH$_2$CH$_2$CH$_2$O—⟨C$_6$H$_4$⟩—OCH$_3$ | |
| 2-99 | H | O—CH$_2$CH$_2$CH$_2$O—⟨C$_6$H$_4$⟩(Bu$^t$ at meta) | |

TABLE 2-continued n = 1:

Structural Formula

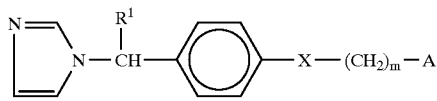

| Compound No. | R¹ | X—(CH$_2$)$_m$—A | Physical Constant |
|---|---|---|---|
| 2-100 | H | O—CH$_2$CH$_2$CH$_2$O—⟨phenyl⟩—Bu$^t$ | |
| 2-101 | H | O—CH$_2$CH$_2$CH$_2$CH$_2$O—⟨phenyl, Bu$^t$ meta⟩ | |
| 2-102 | H | O—CH$_2$CH$_2$CH$_2$CH$_2$O—⟨phenyl⟩—Bu$^t$ | |
| 2-103 | H | NH—CH$_2$CH$_2$O—⟨phenyl⟩—⟨cyclohexyl⟩H | |
| 2-104 | H | O—CH$_2$CH$_2$CH$_2$SO$_2$—⟨phenyl⟩—F | [55–57] |
| 2-105 | H | O—CH$_2$CH$_2$CH$_2$SO$_2$—⟨phenyl⟩—CH$_3$ | [60–62] |
| 2-106 | H | O—CH$_2$CH$_2$CH$_2$NHSO$_2$—⟨phenyl⟩ | |
| 2-107 | H | O—CH$_2$CH$_2$CH$_2$SO$_2$—⟨phenyl⟩—COOCH$_3$ | |
| 2-108 | H | O—CH$_2$CH$_2$CH$_2$SO$_2$—⟨phenyl⟩—COOH | |
| 2-109 | H | C$_9$H$_{19}$ | |
| 2-110 | H | C$_{10}$H$_{21}$ | |
| 2-111 | H | C$_{11}$H$_{23}$ | |
| 2-112 | H | C$_{12}$H$_{25}$ | |
| 2-113 | H | NH—C$_8$H$_{17}$ | |
| 2-114 | H | NH—C$_9$H$_{19}$ | |
| 2-115 | H | NH—C$_{10}$H$_{21}$ | n$_D^{23.4}$1.5162 |
| 2-116 | H | NH—C$_{11}$H$_{23}$ | |
| 2-117 | H | O—C$_8$H$_{17}$ | n$_D^{23.4}$1.5162 |
| 2-118 | H | O—C$_9$H$_{19}$ | |
| 2-119 | H | O—C$_{10}$H$_{21}$ | |
| 2-120 | H | O—C$_{11}$H$_{23}$ | |
| 2-121 | H | SO—C$_8$H$_{17}$ | |

*The physical constant is presented in either the melting point (° C.) or the refractive index. (The same as follows.)

What is claimed is:

1. A compound represented by the formula

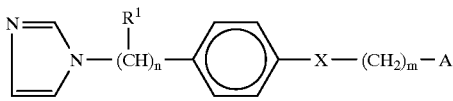  [I]

wherein R¹ is hydrogen, n is 0 or 1, X is O or N-r¹ wherein r¹ is hydrogen or a $C_{1-14}$ alkyl, m is an integer of from a 2 to 12, and A is methyl or a group represented by the following formula:

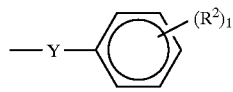

wherein Y is O, S, $SO_2$, $CH_2$, $CH(CH_3)$ or $NHSO_2$, $R^2$ is a halogen, a $C_{1-6}$ alkyl, a $C_{1-6}$ alkoxy, a $C_{3-6}$ cycloalkyl or $COOr^6$ wherein $r^6$ is hydrogen or a $C_{1-4}$ alkyl, and l is 0, 1, 2 or 3, however, m denotes an integer of from 6 to 9 when A is methyl

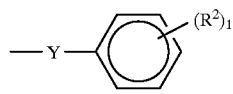

or the pharmaceutically acceptable salts thereof.

2. The compound of claim 1 wherein A is

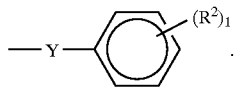

3. The compound of claim 1 wherein R¹ is hydrogen and A is

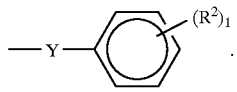

4. The compound of claim 1 wherein X—$(CH_2)_m$—A is

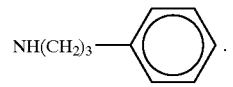

5. The compound of claim 1 wherein X—$(CH_2)_m$—A is

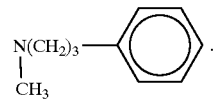

6. The compound of claim 1 wherein X—$(CH_2)_m$—A is

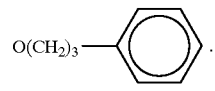

7. The compound of claim 1 wherein X—$(CH_2)_m$—A is

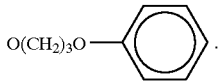

8. The compound of claim 1 wherein X—$(CH_2)_m$—A is

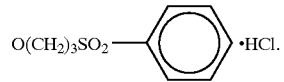

9. The compound of claim 1 wherein X—$(CH_2)_m$—A is NH—$C_{10}H_{21}$.

10. The compound of claim 1 wherein X—$(CH_2)_m$—A is

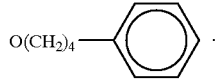

11. The compound of claim 1 wherein X—$(CH_2)_m$—A is

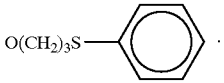

12. The compound of claim 1 wherein X—$(CH_2)_m$—A is

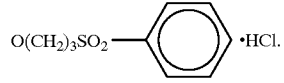

13. The compound of claim 1 wherein X—$(CH_2)_m$—A is

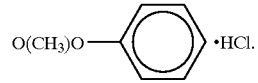

* * * * *